US010086028B2

(12) United States Patent
Park et al.

(10) Patent No.: US 10,086,028 B2
(45) Date of Patent: Oct. 2, 2018

(54) METHOD FOR TREATING VASCULAR INFLAMMATION, IMPROVING SKIN BEAUTY AND IMPROVING MALE SEXUAL FUNCTION USING GINSENG BERRY

(71) Applicant: AMOREPACIFIC CORPORATION, Seoul (KR)

(72) Inventors: Chan-Woong Park, Yongin-si (KR); Myeong Hoon Yeom, Yongin-si (KR); Nam Hoon Cho, Seongnam-si (KR); Sang Jun Lee, Seongnam-si (KR); Sang Min Lee, Yongin-si (KR); Jin Young Lee, Yongin-si (KR); Hee Yong Jeon, Yongin-si (KR); Young-Myeong Kim, Chuncheon-si (KR); Chun-Ki Kim, Chuncheon-si (KR); Young Deuk Choi, Seoul (KR)

(73) Assignee: AMOREPACIFIC CORPORATION, Seoul (KR)

( * ) Notice: Subject to any disclaimer, the term of this patent is extended or adjusted under 35 U.S.C. 154(b) by 388 days.

(21) Appl. No.: 14/274,243

(22) Filed: May 9, 2014

(65) Prior Publication Data

US 2014/0248380 A1 Sep. 4, 2014

Related U.S. Application Data

(60) Division of application No. 13/565,224, filed on Aug. 2, 2012, now Pat. No. 9,314,493, which is a continuation-in-part of application No. 12/602,457, filed as application No. PCT/KR2008/002996 on May 28, 2008, now abandoned.

(30) Foreign Application Priority Data

May 28, 2007 (KR) ........................ 10-2007-0051593
May 9, 2008 (KR) ........................ 10-2008-0043488

(51) Int. Cl.
*A61K 36/258* (2006.01)
*A61Q 19/08* (2006.01)
*A61K 8/97* (2017.01)
*A61K 31/198* (2006.01)
*A61Q 19/02* (2006.01)

(52) U.S. Cl.
CPC .............. *A61K 36/258* (2013.01); *A61K 8/97* (2013.01); *A61K 31/198* (2013.01); *A61Q 19/02* (2013.01); *A61Q 19/08* (2013.01)

(58) Field of Classification Search
CPC .................................................. A61K 36/258
See application file for complete search history.

(56) References Cited

U.S. PATENT DOCUMENTS

| 6,444,237 B1 | 9/2002 | Heleen |
| 6,524,626 B2 | 2/2003 | Chen |
| 2002/0012644 A1 | 1/2002 | Chen |
| 2003/0152544 A1 | 8/2003 | Chen |
| 2006/0198908 A1 | 9/2006 | Ko |
| 2008/0267938 A1 | 10/2008 | Olalde Rangel |

FOREIGN PATENT DOCUMENTS

| CN | 1242374 A | 1/2000 | |
| CN | 1440691 | 9/2003 | |
| CN | 1628683 A | 6/2005 | |
| CN | 1690071 A | 11/2005 | |
| CN | 1732963 | 2/2006 | |
| CN | 1958595 A | 5/2007 | |
| JP | 62-263130 A | 11/1987 | |
| JP | 10-000070 A | 1/1988 | |
| JP | 07-267977 A | 10/1995 | |
| JP | 07267977 A | * 10/1995 | |
| JP | 2000-212080 | 8/2000 | |
| JP | 2002-541872 A | 12/2002 | |
| JP | 2003-503012 A | 1/2003 | |
| JP | 2003-527304 A | 9/2003 | |
| JP | 2005-289913 A | 10/2005 | |
| JP | 2005-306806 | 11/2005 | |
| JP | 2008-100999 | 5/2008 | |
| KR | 10-2001-0074683 | 8/2001 | |
| KR | 10-2007-0032435 A | 3/2007 | |
| KR | 10-0780056 B1 | 11/2007 | |
| KR | 10-0823940 B1 | 4/2008 | |
| WO | WO-03086440 A1 | * 10/2003 | ............... A23L 2/52 |
| WO | WO 2005/016362 | 2/2005 | |
| WO | WO 2006/115307 A1 | 11/2006 | |
| WO | WO 2007/061182 A1 | 5/2007 | |

OTHER PUBLICATIONS

Office Action from European Application No. 08 765 961.1 (dated Mar. 24, 2014).
Office Action from Chinese Application No. 201110401145.9 (dated Mar. 27, 2014).
Lee et al., "*Panax gingseng* induces human Type I collagen synthesis through activation of Smad signaling", *Journal of Ethnopharmacology*, 109(1): 29-34 (2006).
Wang et al., "A review of the Studies on Chemical Constituents and Pharmaceutical Activities of the Fruit of Panax ginseng", *Journal of Jilin Agricultural University*, 27(1): 71-75, 78 (2005).
Kim et al., "Effects of Red Ginseng Powder and Silk Peptide on Hypercholesterolemia and Atherosclerosis in Rabbits", *Lab. Anim. Res.*, 24(1):67-75 (2008), Abstract.
Office Action from Japanese Patent Application No. 2014-023781 (dated Feb. 10, 2015).
Office Action from Japanese Patent Application No. 2014-023806 (dated Feb. 10, 2015).
Office Action from Korean Patent Application No. 10-2008-0119781 (dated Jan. 21, 2015).

(Continued)

*Primary Examiner* — Amy L Clark
(74) *Attorney, Agent, or Firm* — Merchant & Gould P.C.

(57) ABSTRACT

The present disclosure discloses a method for treating vascular inflammation, improving skin beauty and improving male sexual function of a subject by administering a ginseng berry extract to the subject.

2 Claims, 31 Drawing Sheets

(56) References Cited

OTHER PUBLICATIONS

Office Action from Japanese Patent Application No. 2014-143436 (dated Jun. 9, 2015).
www.mayoclinic.com/health/arteriosclerosis-atherosclerosis/DS00525/METHOD=print&Dsection=all (accessed Dec. 2011).
Kang et al, "Ginsenosides of the protopanaxatriol group gause endothelium-dependent relaxation in the RAT aorta," *Life Sciences*, 56(19):1577-86 (1995).
Leung et al, "Non-genomic effects of ginsenoside-Re in endothelial cells via glucocorticoid receptor," *FEBS Letters*, 581:2423-28 (2007).
Korea Ginseng and Tobacco Research Institute, "Cultivation of Ginseng," *The Recent Korean Ginseng: Cultivation* (1996) 130-131.
Korea Ginseng and Tobacco Research Institute, "Chemical Composition of Ginseng," *The Recent Korean Ginseng: Constituents & Effects* (1996) 56-112.
Seizi, "Hypoxia and No gene expression," *The way of medicine*, 195:815-16 (2000).
Wang et al. "In vitro anti-cancer activity and structure-activity relationships of natural products isolated from fruits of Panax ginsing," *Cancer Chem. Pharmacol*, 59:589-601 (2007).
Xie et al., "Anti-hyperglycemic effect of the polysaccharides fraction from American ginseng berry extract in ob/ob mice," *Phytomedicine*, 11:182-87 (2004).
Yue et al. "Elucidation of the mechanisms underlying the angiogenic effects of ginsenoside $Rg_1$ in vivo and in vitro," *Angiogenesis*, 8:205-16 (2005).
Zhao et al., "Effects of IGFS on blood lipid metabolism in experimental hyperlipidemia rats," *Journal of Jilin University (Medicine Edition)*, 31(3):407-10 (2005).
Written Opinion (Form PCT/ISA/237) for PCT Application No. PCT/KR2009/0007010.
Jeong et al., "Therapeutic Angiogenesis," *Journal of Korean Society for Vascular Surgery* (2000) 16 (2): 265-269.
Crossman, D.C., "More problems with the endothelium," *Q. J. Med.* (1997) 90: 157-160.
Chuang et al., "eGMP mediates corpus cavernosum smooth muscle relaxation with altered cross-bridge function," *Life Sciences* (1998) 63 (3): 185-194.
Minghetti et al., "Inductible nitric oxide synthase expression in activated rat microglial cultures is downregulated by exogenous prostaglandin $E_2$ and by cyclooxygenase inhibitors," *GLIA* (1997) 19: 152-160.
Dooley et al., "Development of an in vitro primary screen for skin depigmentation and antimelanoma agents," *Skin Pharmacol* (1994) 7 (4): 188-200. Abstract Only.
Shao et al., "Antioxidant effects of American ginseng berry extract in cardiomyocytes exposed to acute oxidant stress," *Biochimica et Biophysica* (2004) 1670: 165-171.
Kang et al., "Ginsenosides of the protopanaxatriol group cause endothelium-dependent relaxation in the rat aorta," *Life Sciences* (1995) 56 (19): 1577-1586.
Yue et al., "Elucidation of the mechanisms underlying the angiogenic effects of ginsenoside $Rg_1$ in vivo and in vitro," *Angiogenesis* (2005) 8: 205-216.
Folkman et al., "Angiogenesis" *The Journal of Biological Chemistry* (1992) 267 (16): 10931-10934.
Simonsen et al., "Nitric oxide is involved in the inhibitory neurotransmission and endothelium-dependent relaxation of human small penile arteries," *Clinical Science* (1997) 92: 269-275.
Chen et al., "Ginsenosides-induced nitric oxide-mediated relaxation of the rabbit corpus cavernosum," *British Journal of Pharmacology* (1995) 115: 15-18.
Wang et al., "Saponins composition in American ginseng leaf and berry assayed by high-performance liquid chromatography," *Journal of Agricultural and Food Chemistry* (2006) 54: 2261-2266.
Dey et al., "Anti-hyperglycemic effects of ginseng: Comparison between root and berry," *Phytomedicine* (2003) 10: 600-605.
Forte et al., "Basal nitric oxide synthesis in essential hypertension," *The Lancet* (1997) 349: 837-842.
Leung et al., "Non-genomic effects of ginsenoside-Re in endothelial cells via glucocorticoid receptor," *FEBS Letters* (2007) 581: 2423-2428.
Attele et al., "Ginseng Pharmacology—Multiple constituents and multiple accents," *Biochemical Pharmacology* (1999) 58: 1685-1693.
Xie et al., "The anti-hyperglycemic property of different ginseng partitions," *Oriental Pharmacy and Experimental Medicine* (2005) 5 (1): 1-15.
Ryu et al., "Free radical-scavenging activity of Korean Red Ginseng for erectile dysfunction in non-insulin-dependent diabetes mellitus rats," *Urology* (2005) 65 (3): 611-615. ISSN: 0090-4295.
Xie et al., "Constituents and effects of ginseng leaf," *Oriental Pharmacy and Experimental Medicine* (2004) 4 (1): 1-8.
Lee et al., "Antioxidant activities of leaf, steam and root of *Panax ginseng* C. A. Meyer," *Korean J. Medicinal Crop Sci.* (2004) 12 (3): 237-242.
Park et al., "Biological activities and chemistry of saponins from *Panax ginseng* C.A. Meyer," *Phytochemistry Reviews* (2005) 4: 159-175.
Nam et al., "Relationship of saponin and non-saponin for the quality of ginseng," *J. Ginseng Res.* (1998) 22 (4): 274-283.
Hwang et al., "Quantitative analysis of phenolic compounds in different parts of *Panax ginseng* C.A. Meyer and it's inhibitory effect on melanin biosynthesis," *Korean J. Medicinal Crop Sci.* (2006) 14 (3): 148-152.
Third Party Observation for corresponding EP Patent Application No. 08765961.1 and cited art—Kaiyadeva; Kaiyadevanighantau—(Pathyapathyavibodhakah) Edited and translated by P.V. Sharma and Guru Prasad Sharma, Chaukhambha Orientalia, Varanasi, $1^{st}$ Edition, 1979, p. 642.
Wu et al., "Effects of ginseng fruit saponins (GFS) on coronoary circulation and myocardial oxygen metabolism in dogs with acute myocardial infraction," *Journal of Jilin University (Medicine Edition)* (2006) 32 (3): 428-431.
Xu et al., "Study on the chemical components of ginseng fruit," *Chinese Traditional and Herbal Drugs* (2007) 38 (5): 667-669.
Office Action for corresponding Chinese application No. 2008800181983.9 dated Jul. 12, 2011.
Choi et al., "Effect of Extraction on Chemical Composition of Red Ginseng Extract," *Korean J. Ginseng Sci.*, vol. 4, No. 1, 1980, pp. 88-95.
Chinese Office Action for Chinese Patent Application No. 200880018198.9 dated Jun. 5, 2012. (English Translation).
Attele et al., "Antidiabetic Effects of *Panax ginseng* Berry Extract and the Identification of an Effective Component", *Diabetes*, vol. 51, No. 6, 2002, pp. 1851-1858.
Extended European Search Report for European Application No. 09829329.3 dated Jan. 28, 2013.
Extended European Search Report for European Application No. 08765961.1 dated Mar. 8, 2013.
Mehendale et al., "Chronic pretreatment with American ginseng berry and its polyphenolic constituents attenuate oxidant stress in cardiomyocytes", *European Journal of Pharmacology*, vol. 553, 2006, pp. 209-214.
Nam et al., "Inhibition of cytokine-induced IκB kinase activiation as a mechanism contributing to the anti-atherogenic activity of tilianin in hyperlipidemic mice", *Atherosclerosis*, vol. 180, 2005, pp. 27-35.
Office Action for Chinese Patent Application No. 201110401114.3 dated Feb. 5, 2013.
Office Action for Chinese Patent Application No. 201110401145.9 dated Feb. 27, 2013.
Peng et al., "Antihyperglycemic effects of ginseng and possible mechanisms", *Drugs of the Future*, vol. 33, No. 6, 2008, pp. 507-514.
Yushu et al., "Clinical Study of the Anti-aging Effect of Ginseng Berry Saponin", *Journal of Traditional Chinese Medicine*, No. 10, 1983, pp. 39-41 (English Abstract).

(56) References Cited

OTHER PUBLICATIONS

Jang Soo Chun, "Ginseng fruit chemistry, pharmacology of recent research", *Special Experimental Obstetrics*, vol. 2, 1984, pp. 32-35 (Abstract).
Office Action from Chinese Patent Application No. 200980155347.0 dated Mar. 1, 2013.
Zhang et al., "Ginsenoside Rg1 Inhibits Tumor Necrosis Factor-α (TNF-α)-Induced Human Arterial Smooth Muscle Cells (HASMCs) Proliferation", *Journal of Cellular Biochemistry*, 98:1471-81 (2006).
Koyama et al., "Inhibitory Effect of Ginsenosides on Migration of Arterial Smooth Muscle Cells", *American Journal of Chinese Medicine*, 20(2):167-73 (1992).
Zhang et al., "Effects of ginsenoside-Rb on blood lipid metabolism and anti-oxidation in hyperlipidemia rats", *China Journal of Chinese Materia Medica*, 29(11):1085-88 (2004).
Japanese Office Action for Japanese Application No. 2011-538548 dated Jun. 11, 2013.
Choi, "Botanical characteristics, pharmacological effects and medicinal components of Korean *Panax ginseng* C A Meyer," *Acta Pharmacol Sin*, 29(9):1109-18 (2008).
Kim et al., "Ginseng Berry Extract Prevents Atherogenesis via Anti-Inflammatory Action by Upregulating Phase II Gene Expression," *Evidence-Based Complementary and Alternative Medicine*, vol. 2012, Article ID 490301, pp. 1-14 (2012).
Office Action from U.S. Appl. No. 13/131,007 (dated Aug. 1, 2013).
Shao et al., "Antioxidant effects of American ginseng berry extract in cardiomyocytes exposed to acute oxidant stress," *Biochimica et Biophysica Acta*, 1670:165-71 (2004).
Leung et al., "Non-genomic effects of ginsenoside-Re in endothelial cells via glucocorticoid receptor," *FEBS Letters*, 581:2423-28 (2007).
Shi et al., "Investigation of ginsenosides in different parts and ages of *Panax ginseng*", *Food Chemistry*, 102:664-68 (2007).
Office Action from corresponding Korean Patent Application No. 10-2007-0051593 (dated Sep. 13, 2013).
International Search Report (Form PCT/ISA/210) for International Application No. PCT/KR2009/007010 (dated Jul. 16, 2010).
Written Opinion (Form PCT/ISA/237) for International Application No. PCT/KR2009/007010 (dated Jul. 16, 2010).
Moody et al., "Effects of long-term oral administration of L-arginine on the rat erectile response", *J. Urol.*, 158(3 Pt 1):942-947. (1997) Abstract Only.
Office Action from Korean Patent Application No. 10-2013-0155424 (dated Apr. 4, 2014).
Kim et al. "Multiple Functional Effects of Korea Ginseng on Vascular Endothelial Cells," *Spring Symposium of Academy of Korea Ginseng*, 5:13-17 (2006).
Office Action from Chinese Patent Application No. 201410708650.1 (dated Jul. 11, 2017).
Sun Yan Jun, Study on Nonsaponin of Panax ginseng Berry, E057-98, abstract, pp. 11, 16-17 (2006).

* cited by examiner

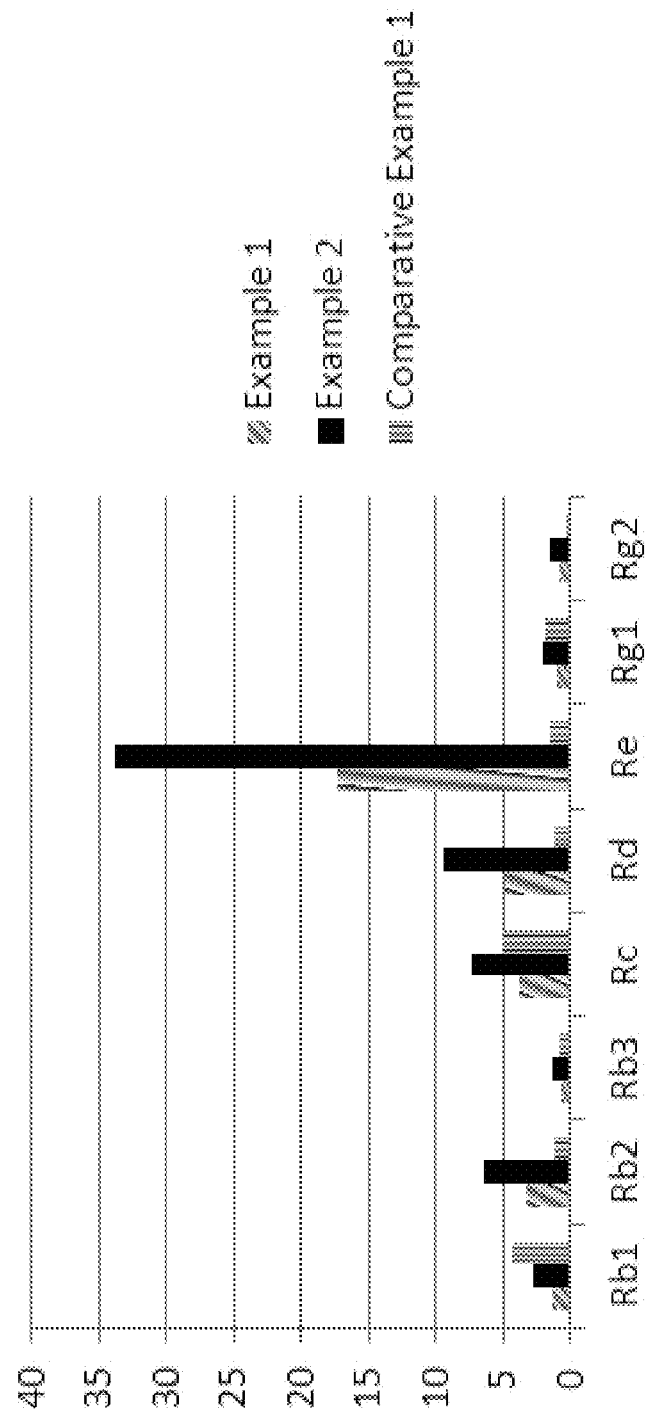

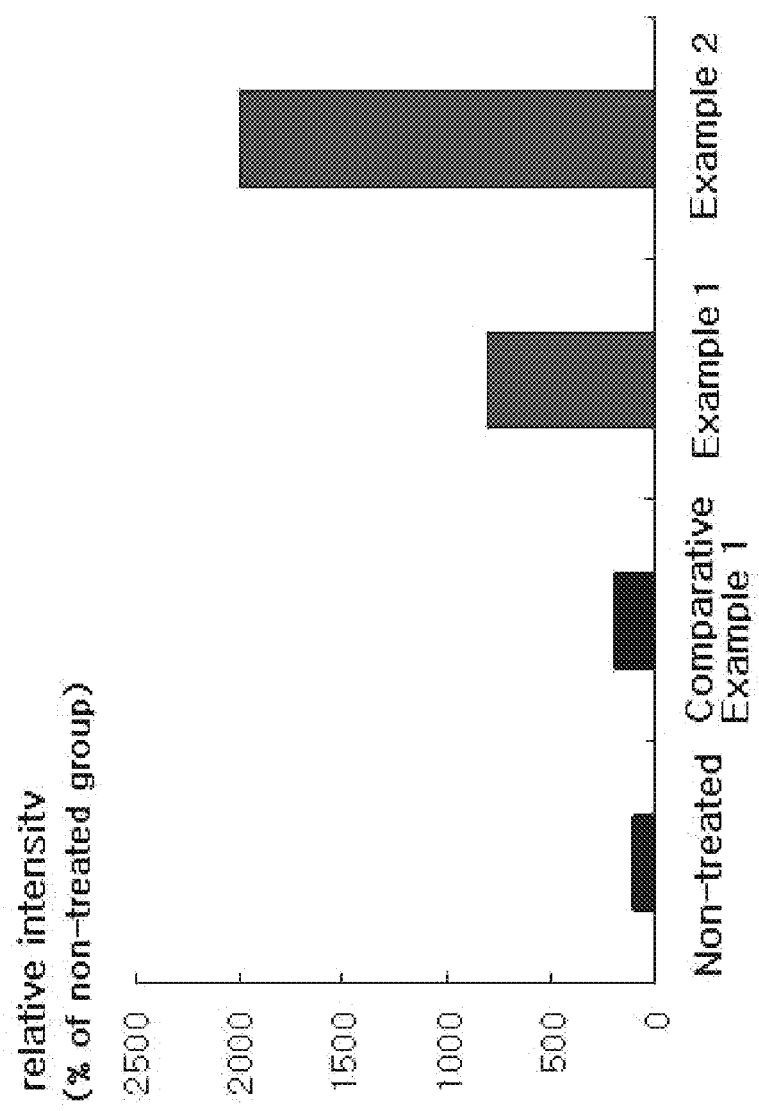

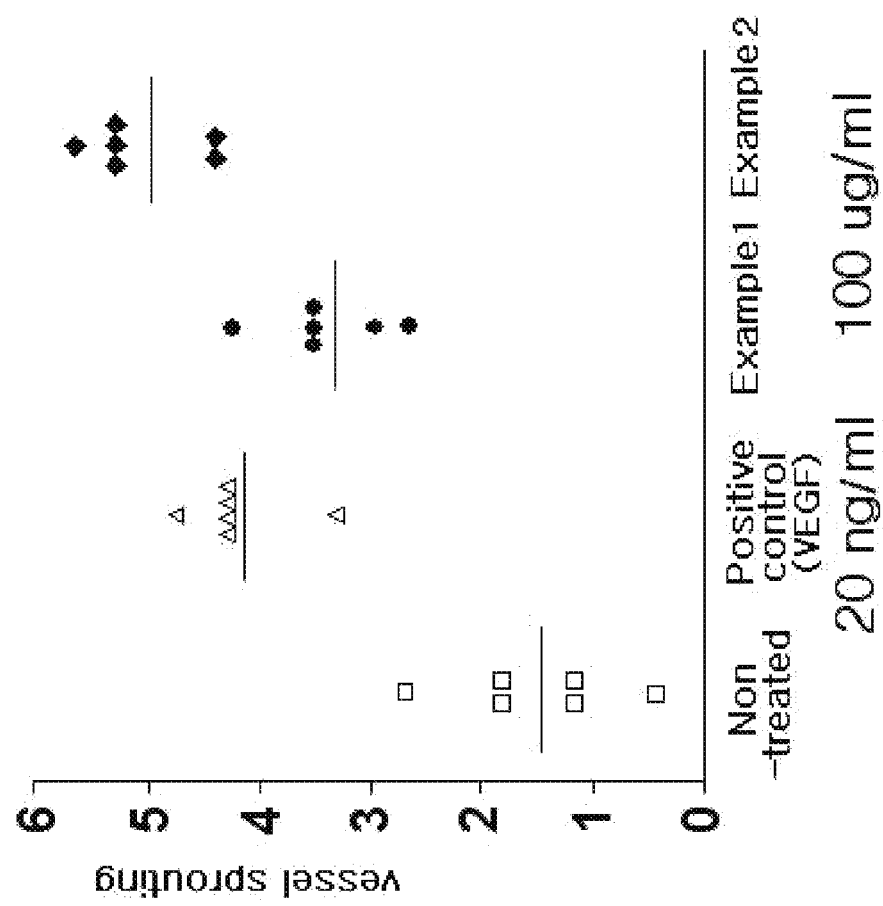

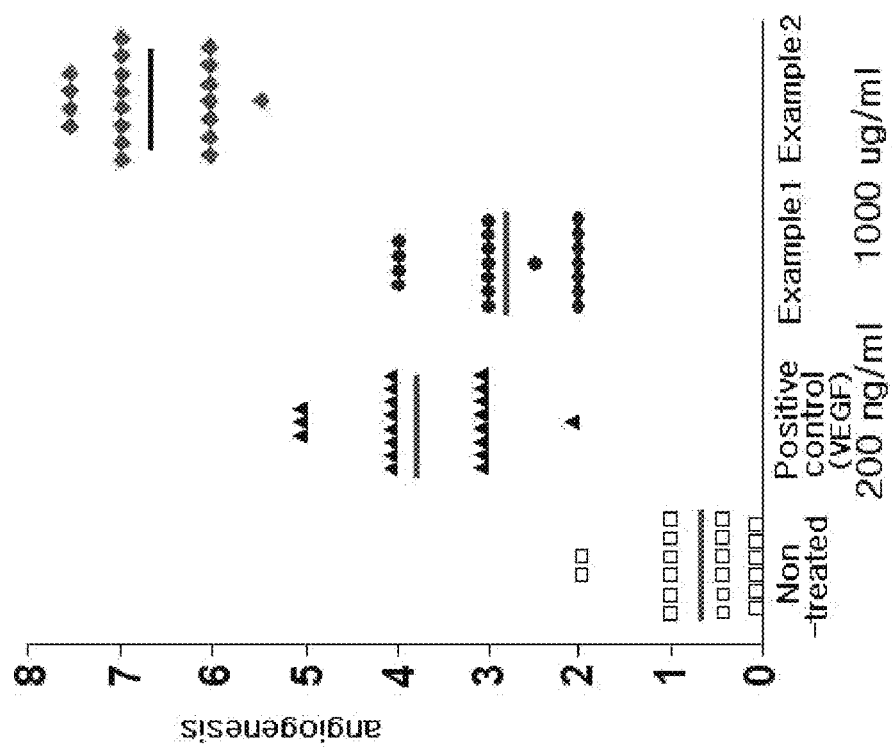

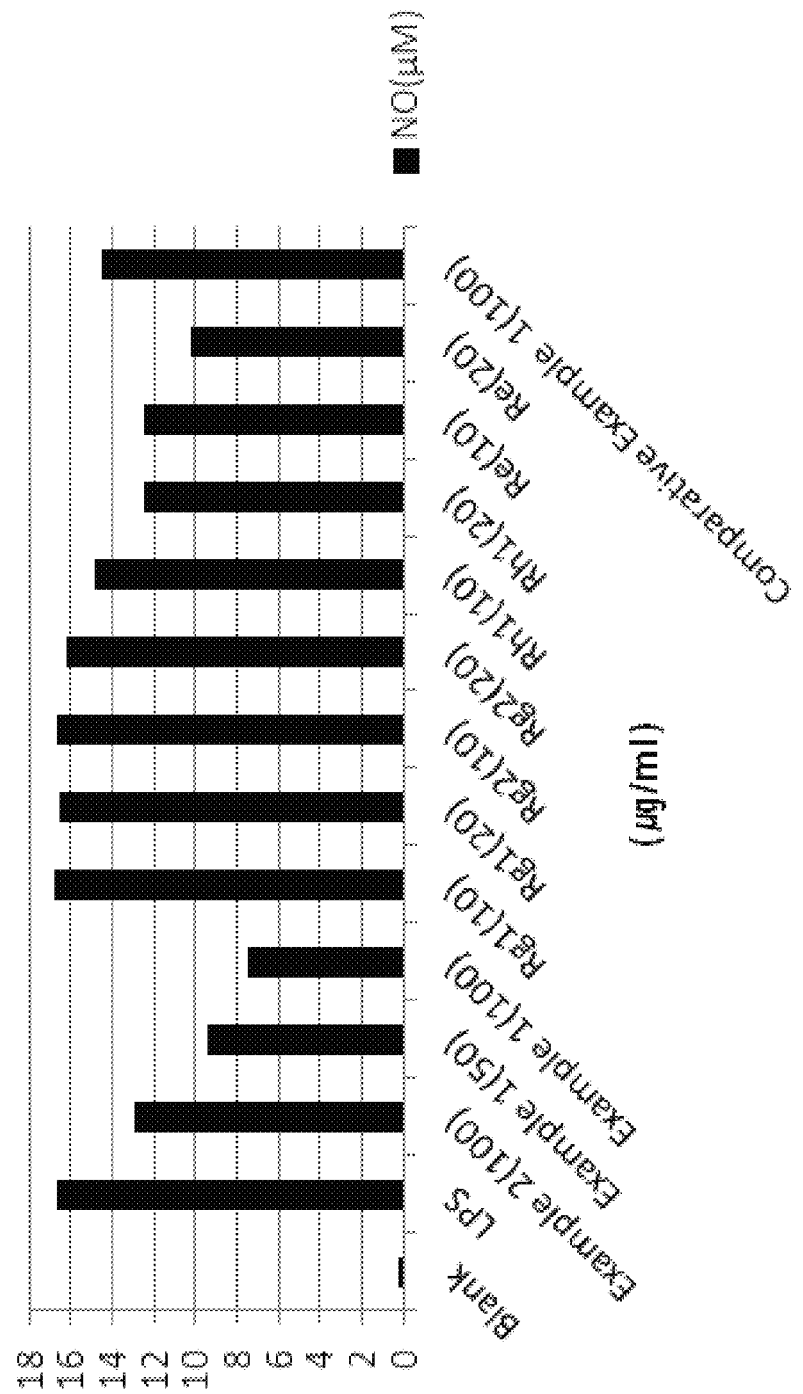

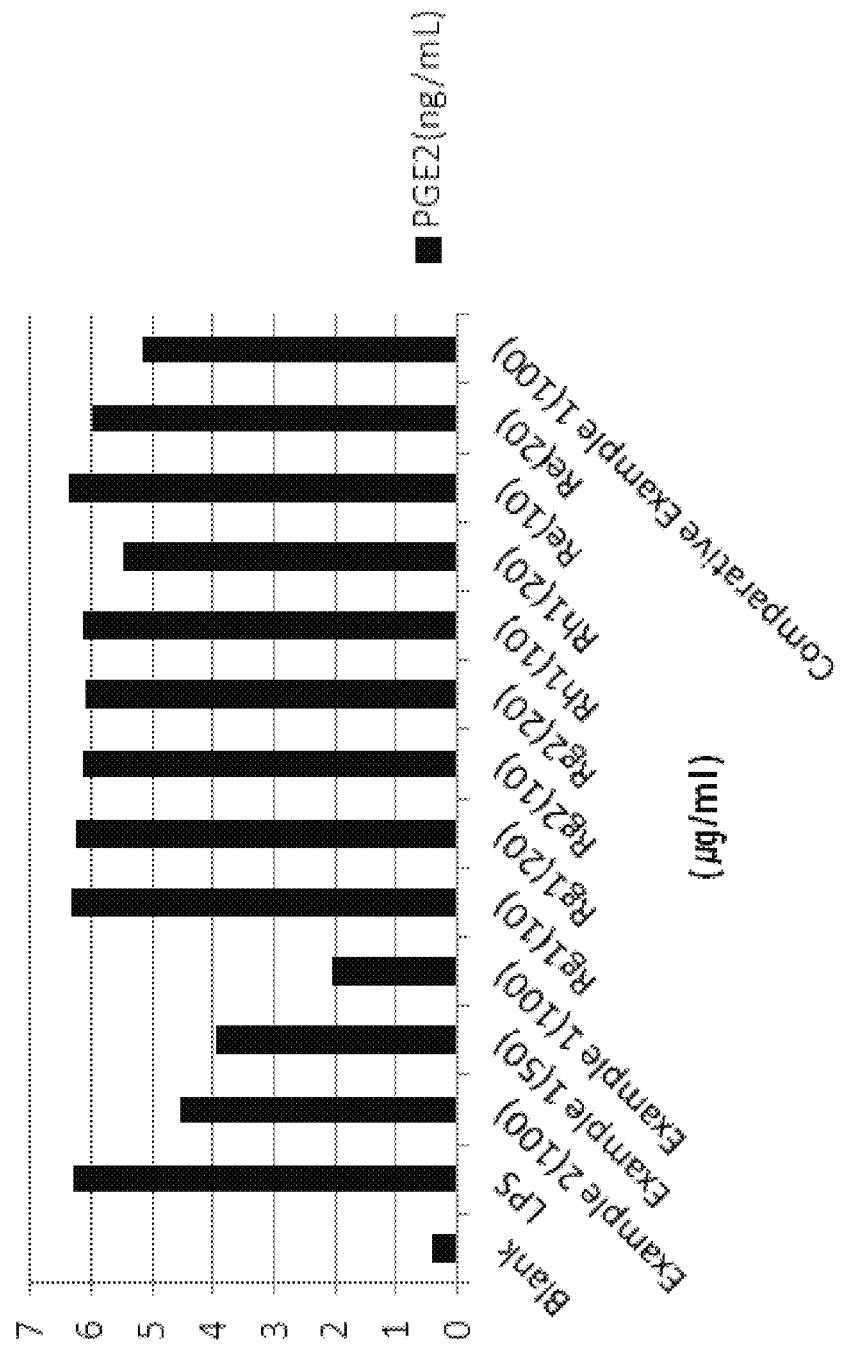

METHOD FOR TREATING VASCULAR INFLAMMATION, IMPROVING SKIN BEAUTY AND IMPROVING MALE SEXUAL FUNCTION USING GINSENG BERRY

CROSS-REFERENCE TO RELATED APPLICATION

This application is a divisional of U.S. patent application Ser. No. 13/565,224 filed Aug. 2, 2012, which is a continuation-in-part of U.S. patent application Ser. No. 12/602,457 filed May 12, 2010, which is a U.S. National Stage Application under 35 U.S.C. § 371 of International Patent Application No. PCT/KR2008/002996 filed May 28, 2008, which claims the benefit of priority to Korean Patent Application No. 10-2007-0051593 filed May 28, 2007, and Korean Patent Application No. 10-2008-0043488 filed May 9, 2008, all of which are hereby incorporated by reference in their entireties. To the extent appropriate, a claim of priority is made to all of these applications.

BACKGROUND

1. Field

The present disclosure relates to a method for treating vascular inflammation, improving skin beauty and improving male sexual function by administering a ginseng berry extract to a subject.

2. Description of the Related Art

P Ginseng (Panax ginseng C. A. Meyer) is a plant belonging to the genus Panax, in the family Araliaceae, and has been used as herb from over 2,000 years in Korea, China, Japan and other countries. Empirically, it has been used to prevent diseases and extend life span. Until now, ginseng is known to have the following effects: positive effect on the central nervous system, anti-carcinogenetic effect, anticancer activity, immune function control, antidiabetic effect, liver function improving effect, improvement of cardiovascular disorder, anti-arteriosclerotic effect, blood pressure control, improvement of climacterium, improvement of osteoporotic conditions, anti-stress and anti-fatigue effects, antioxidative effect, aging prevention effect, and the like [The Recent Korean Ginseng: Constituents and Effects, Korea Ginseng and Tobacco Research Institute, 56-112, 1996].

Ginsenosides, which are typical active compounds of ginseng, are uniformly distributed in aerial and underground parts of the plant. Particularly, it is known that not only contents but also compositions of ginsenosides are different depending on parts from ginseng root to ginseng leaf to ginseng berry (Attele A S et al, Biochem. Pharmacol., 58; 1685-1693, 1999). Among them, ginseng berry is reported to provide superior antidiabetic effect to ginseng root, with characteristic content and composition of ginsenosides (Dey L. et al., Phytomedicine, 10; 600-605, 2003).

From old times, ginseng berry has been valued more preciously than other parts of ginseng. It has been selected and harvested to obtain seeds. Seed gathering from ginseng berry is carried out only once in 4-year-old ginseng. It is difficult to produce good yearlings from 3-year-old ginseng, because the seeds are too small. Seeds gathered from ginseng 5 or more years old are robust, but the ginseng root may not grow sufficiently, and it is difficult to produce high-quality red ginseng because the tissue is not so dense. And, if seed gathering is carried out 2 or more times, quantity and quality of red ginseng are impaired significantly [The Recent Korean Ginseng: Cultivation, Korea Ginseng and Tobacco Research Institute, 130-131, 1996].

With regard to blood circulation, dilation of capillaries is essential particularly in peripheral blood circulation. That is, dilation of the blood vessels is necessary for increase of blood flow in the blood vessels. Nitric oxide (NO) generated by the action of endothelial nitric oxide synthase (eNOS) is involved in the dilation of blood vessels. Therefore, in case of hypertension, generation of NO decreases [Forete, P. et al., Basal nitric acid synthesis in essential hypertension. Lancet. 1997; 349:837-842]. Also, other factors such as aging, smoking, hyperlipidemia and diabetes reduce NO generation in blood vessels [Crossman, D C. More problems with endothelium. Q J Med. 1997; 90: 157-160].

Angiogenesis is a process involving the growth of new blood vessels from pre-existing vessels. It occurs in several stages including migration of endothelial cells constituting blood vessels, invasion through the extracellular matrix (ECM), which is an inter-cellular barrier, proliferation, and differentiation into blood vessels (tube formation) [Folkman, J. et al., Angiogenesis. The Journal of Biological Chemistry, 1992, 267(16), 10931-10934].

Physiologically, angiogenesis occurs during embryonic development or menstruation and may occur temporarily due to local oxygen deficiency. Therapeutic angiogenesis is utilized in case blood supply is insufficient as in ischemic disease, bone fracture or the like. Worldwide, ischemic cardiovascular diseases caused by arteriosclerosis are among the major causes of death, and they are increasing fast in Korea, too [Jeong, Jin-Ok et al., Therapeutic angiogenesis. Journal of Korean Society for Vascular Surgery. 2000. 16(2), 265-269).

L-Arginine is a basic amino acid with chemical formula $C_6H_{14}N_4O_2$ and molecule weight 174.21. It was first isolated from a lupine (a kind of bean) seedling extract. L-Arginine is one of the amino acids constituting proteins. It is rich in the protein protamine, which exists in the sperm of fish, and exists in free state in plant seeds. Further, it is a major component in the urea cycle (also known as the ornithine cycle). By the action of the enzyme arginase, it is decomposed into urea and ornithine. It is synthesized from citrulline and aspartic acid. Although L-arginine is a nonessential amino acid for adults, it is nutritionally essential for infants.

NO-nitro-L-arginine is known as an inhibitor of nitric oxide synthase. Researches show that NO-nitro-L-arginine may interfere with the relaxation of blood vessels. However, other researches show that the inhibition effect of NO-nitro-L-arginine can be reversed in the presence of L-arginine ($3 \times 10^{-3}$ mol/L) [Simonsen et al., NO is involved in the inhibitory neurotransmission and endothelium-dependent relaxations of human small penile arteries, Clin. Sci. 92:3, 265-75.]. This research asserts that L-arginine can be an effective substrate for nitric oxide synthase and can stimulate release of free NO in blood vessels.

The aspects of male sexual function include sexual desire, penile erection, ejaculation and orgasm. This sexual function is determined by complicated physiological interactions of the nervous, endocrine and blood circulatory systems. A disorder in any of them may result in sexual dysfunction. Until just about 10 years ago, sexual dysfunction has been considered to result from psychogenic reasons. However, with the development of modern medical science, it has been found that sexual dysfunction in about 50% of patients is caused by various reasons including disorders in the blood circulatory, nervous and endocrine systems, diabetes, hypertension, drug intake, and the like. Recently, sildenafil, which is an inhibitor of phosphodiesterase V, is drawing a lot of interests with respect to treatment of sexual dysfunction. But, this therapy merely induces erection temporarily using a chemical, and is costly and associated with a lot of adverse reactions, including headache, increased blood pressure, heart attack, and the like. Especially, not a few death cases associated with heart attack are reported. Accordingly, a safe and effective treatment that can fundamentally enhance the erectile function is required. The recent trend is toward the development of sexual dysfunction treatment which increases the production of NO and cGMP, which are signal transduction substances that induce strong relaxation of the cavernous smooth muscle, and, thereby, enhances penile erection.

The changes occurring during penile erection are complicated and require a highly coordinated control involving the peripheral and central nervous systems and the endocrine system. The contraction of the cavernous smooth muscle is controlled by noradrenergic nerve stimulation through activation of post-synaptic $\alpha_1$ adrenergic receptor, and the erectile dysfunction may be associated with the increased tension of the cavernous smooth muscle. However, relaxation of the penile smooth muscle is mediated in part by the non-adrenergic, non-cholinergic (NANC) neurotransmission, and the decrease of tension of the penile cavernous smooth muscle is caused by the relaxation of the corpus cavernosum by NO. During sexual excitement, NO is released from neurons and endothelial cells, binds with soluble guanylate cyclase (sGC) existing in smooth muscle cells and endothelial cells and activate it, and, thereby, increases the level of cyclic guanosine 3'-,5'-monophosphate (cGMP) in the cells. Through unknown mechanism, although it is believed that activation of protein kinase G is associated, the increased cGMP level induces the relaxation of the corpus cavernosum by reducing calcium level in the cells (it is probable that it is caused by the activation of $Ca^{2+}$-activated $K^+$-channel) [Chuang et al., cGMP mediates corpus cavernosum smooth muscle relaxation with altered cross-bridge function. *Life Sci.* 1998; 63(3):185-94].

As the standard of living is improved and people are more concerned with appearance, desires of improving skin beauty with edible products, not only with cosmetics applied on the skin, are increasing greatly. That is, concerns and expectations about skin beauty foods which are effective in preventing skin aging, improving wrinkles, and providing skin whitening and skin moisturizing effects are increasing.

Skin is the organ that covers our body. It is composed of three primary layers: the epidermis, the dermis, and the hypodermis. There are other accessory organs such as sweat glands, sebaceous glands, mammary glands, hair follicles, and the like. The epidermis is further subdivided into the following strata: corneum, lucidum, granulosum, spinosum and basale. The main types of cells which make up the epidermis are keratinocytes and melanocytes. The dermis is divided into two areas: a superficial area called the papillary region, and a deep thicker area known as the reticular region. It is composed of viscoelastic tissues, and is made up of amorphous matrices and fibrous proteins like collagen, elastin and the like. The papillary region is made up of fine collagen fibers and voids between them, and is rich in cellular components and matrix components. On the other hand, the reticular region is made up of thick and aggregated collagen fibers and voids between them. The collagen fibers are linked by elastin.

Skin aging can be classified into intrinsic aging and extrinsic aging depending on its cause. Intrinsic aging is the degradation of structure and physiological functions of the skin with time, regardless of environmental change. Extrinsic aging is caused by prolonged exposure to external environment such as sunlight. Especially, skin aging caused by light is called photoaging. Ultraviolet (UV) light is the main cause of physiological and morphological changes in skin aging. In addition to the intrinsic and extrinsic aging factors, environmental effects of the modern society and seasonal factors result in decreased biosynthesis of hyaluronic acid, which is the main component of glycoproteins in the epidermis and the dermis. As a result, the skin becomes rough and dry.

If intrinsic skin aging proceeds, the skin becomes dry, while fine wrinkles increase and deepen. Further, because of structural and functional changes of the epidermis, the dermis, and the like, the skin loses much of its elasticity and looks drooping. The dermis becomes thinner, whereas the total quantity of collagen is lost 1% each year, and the remaining collagen fibers gradually become thicker and tend to crosslink, resulting in reduced solubility, elasticity and the like. At the same time, elastin fibers become thicker and tend to crosslink, too. In addition, proliferation of fibroblasts in the dermis decreases, and so does the ability of collagen synthesis and decomposition.

Collagen is the main component of skin tissue related with skin aging. The protein accounts for 77% of the total dry weight of the skin, excluding fats, and accounts for 90% of the fibrous components of the dermis. It is responsible for maintaining skin strength, elasticity and flexibility. Accordingly, facilitation of collagen synthesis and inhibition of collagen degradation have become the major issue with regard to skin beauty and prevention of skin aging.

Photoaging is apparently similar to intrinsic aging, but, histologically, it is associated with thickening of the epidermis because of increased keratinocyte proliferation, increase of melanocytes, and pigmentation at the area damaged by light.

To have clear, transparent and white skin is one of the strong desires of the modern people. Human skin color is determined by the concentration and distribution of melanin in the skin. In addition to hereditary factors, environmental or physiological factors, such as UV, fatigue, stress and the like, are related. Melanin is synthesized as follows. The amino acid tyrosine is turned into DOPA and then to dopaquinone by the action of the enzyme tyrosinase. Then, dopaquinone is converted to melanin through non-enzymatic oxidation. Excessive synthesis of melanin in the skin leads to dark skin, chloasma and freckles. Accordingly, skin whitening effect can be attained by inhibiting the synthesis of melanin in the skin.

SUMMARY

The present disclosure is directed to solve the aforesaid problems. The inventors of the present disclosure have found out that the extract of ginseng berry, which is an aerial part of ginseng, has different composition from the extract of commonly used ginseng root and has better effect.

In an aspect, the present disclosure provides a method for treating vascular inflammation of a subject, comprising administering an effective amount of a ginseng berry extract to the subject. In addition, the present disclosure provides a method for facilitating blood circulation, preventing vascular aging, facilitating blood vessel formation, treating ischemic heart disease and treating local blood insufficiency of a subject by administering an effective amount of a ginseng berry extract to the subject.

In another aspect, the present disclosure provides a method for improving skin beauty of a subject comprising administering an effective amount of a ginseng berry extract to the subject by preventing skin aging, improving skin wrinkles, and whitening and moisturizing the skin of the subject.

In another aspect, the present disclosure provides a method for improving male sexual function of a male subject comprising administering an effective amount of a ginseng berry extract to the subject by increasing generation of nitric oxide (NO), which is a signaling substance that provides strong relaxation of the smooth muscle of the corpus cavernosum, and enhancing penile erection.

When an effective amount of a ginseng berry extract is applied to a subject in accordance with the present disclosure, vascular inflammation of the subject may be treated by inhibiting NO generation induced by LPS as well as generation of inflammatory factors such as PGE2, TNF-α and IL1-β, blood circulation of the subject may be facilitated by dilating blood vessels, vascular aging of the subject may be inhibited by increasing viability of endothelial cells and facilitating differentiation and migration of the endothelial cells, ischemic heart disease such as arteriosclerosis, angina and myocardial infarction may be treated, and local blood insufficiency caused by arthritis or bone fracture may be improved and treated.

Further, when an effective amount of a ginseng berry extract is applied to a subject, skin wrinkles of the subject may be improved and at the same time skin aging may be prevented via inhibition of oxidation through scavenging of reactive oxygen species, promotion of procollagen generation, and inhibition of MMP-1 expression, COX-2 biosynthesis and UV-induced TNF-α biosynthesis. Also, when the ginseng berry extract is applied to a subject, superior skin whitening effect can be achieved through inhibited melanin production and excellent skin moisturizing effect can be achieved through facilitated hyaluronic acid generation.

In addition, when an effective amount of a ginseng berry extract is applied to a subject, penile erection can be enhanced and male sexual function of the subject can be improved via increased NO generation in endothelial cells and facilitated relaxation of the penile cavernous smooth muscle. The effect of improving the sexual function of the male subject by the ginseng berry extract may be further enhanced when L-arginine, which is a substrate for nitric oxide synthase, is applied together.

BRIEF DESCRIPTION OF THE DRAWINGS

FIG. 1 compares the composition of ginsenosides in a ginseng berry extract, a ginseng berry saponin concentrate and a ginseng root extract.

FIG. 6b shows vessel sprouting promoting effect evaluated by measuring length and number of newly formed vessels.

FIG. 7b shows blood vessel change analyzed using a computer program (0: fewest changes, 5: most changes).

FIG. 8 compares inhibition of LPS-induced nitric oxide (NO) generation.

FIG. 9 shows generation of the inflammatory factor PGE2 from mouse blood.

DETAILED DESCRIPTION

Figure 2A:
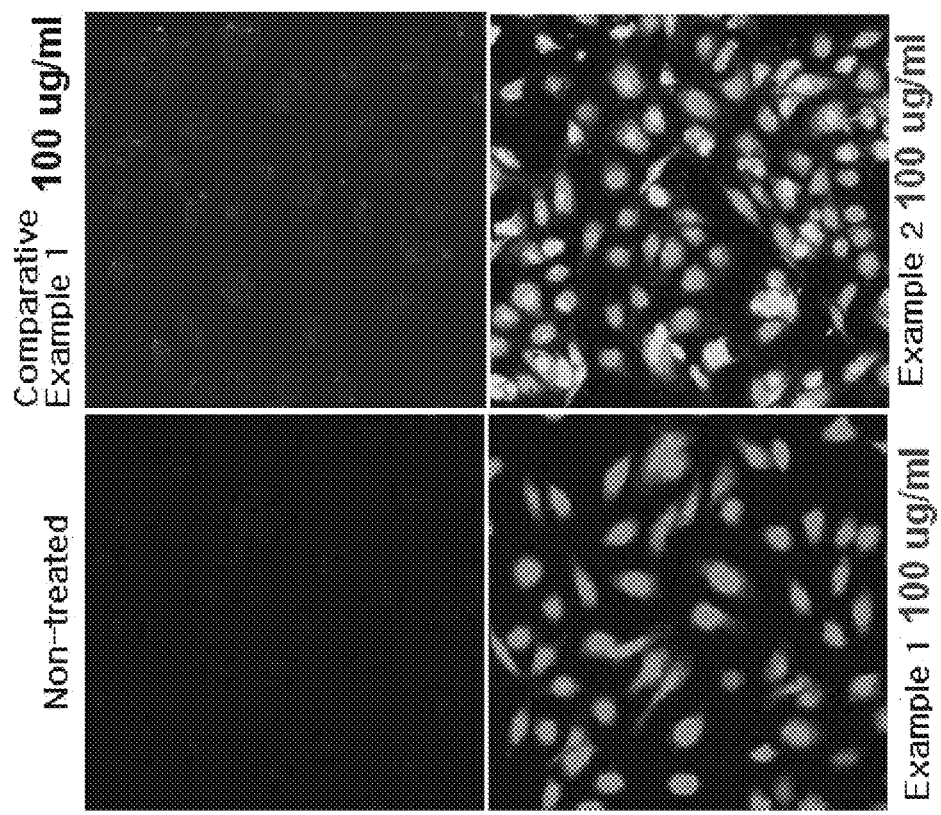
FIG. 2a shows confocal laser microscopic images of endothelial cells, and FIG. 2b compares intensity of fluorescence with that of the non-treated group.

Hereinafter, reference will be made in more detail to the present disclosure.

In an aspect of the present disclosure, an effective amount of a ginseng berry extract may be administered to a subject in the form of a composition. In another aspect of the present disclosure, the ginseng berry extract may be administered to a subject in the form of a pharmaceutical or food composition. In another aspect of the present disclosure, the ginseng berry extract may be administered to a subject via oral or parenteral administration.

In an aspect, the present disclosure provides a composition comprising a ginseng berry extract as an active ingredient.

In another aspect of the present disclosure, the composition includes a composition for treating vascular inflammation, a composition for facilitating blood circulation, a composition for preventing vascular aging, a composition for facilitating blood vessel formation, a composition for treating ischemic heart disease and a composition for improving and treating local blood insufficiency, comprising a ginseng berry extract as an active ingredient. In an aspect of the present disclosure, the ischemic heart disease includes arteriosclerosis, angina or myocardial infarction.

In another aspect of the present disclosure, the composition includes a composition for improving skin beauty, comprising a ginseng berry extract as an active ingredient. In another aspect of the present disclosure, the composition includes a composition for preventing skin aging, improving skin wrinkles and whitening and moisturizing the skin, comprising a ginseng berry extract as an active ingredient.

In another aspect of the present disclosure, the composition includes a composition for improving male sexual function, comprising a ginseng berry extract as an active ingredient. In another aspect of the present disclosure, the composition may further comprise L-arginine.

In an aspect of the present disclosure, the composition may comprise 0.01-100 wt %, specifically 0.5-90 wt %, more specifically 1-80 wt %, of a ginseng berry extract based on the total weight of the composition, depending on the type of the composition. In another aspect of the present disclosure, the composition may comprise 0.01-99.9 wt %, specifically 0.5-80 wt %, more specifically 1-50 wt %, of L-arginine based on the total weight of the composition, depending on the type of the composition. When the ingredients are included within the above range, the effect desired by the present disclosure can be achieved while ensuring both the stability and safety of the composition and good cost-effectiveness.

In an aspect of the present disclosure, the ginseng berry extract may be prepared according to an extract preparation method commonly used in the art. Specifically, it may be prepared by extracting dried ginseng berry by adding $C_1$-$C_5$ alcohol such as methanol, ethanol, propanol, isopropanol, butanol, isobutanol, pentanol or isopentanol, specifically ethanol, followed by filtration and concentration. In another aspect of the present disclosure, the ginseng berry extract may be prepared by extracting dried ginseng berry with the $C_1$-$C_5$ alcohol as described above, filtering and concentrating, removing the oil-soluble components using an organic solvent such as diethyl ether, ethyl acetate, butylene glycol or hexane, extracting again by adding $C_1$-$C_5$ alcohol such as methanol, ethanol, propanol, isopropanol, butanol, isobutanol, pentanol or isopentanol, specifically butanol, and filtering and concentrating.

In order to improve male sexual function, it is required to facilitate penile erection through strong relaxation of the corpus cavernosum. The mechanism is related with increasing generation of nitric oxide (NO). In animal experiments, it was found out that NO plays an important role in penile erection. Upon sexual stimulation, NO generation in endothelial cells increases at the penile parasympathetic periphery. NO activates guanylate cyclase, which converts guanosine triphosphate (GTP) to cyclic guanosine monophosphate (cGMP). The resultant cGMP provides a signal which triggers relaxation of the cavernous smooth muscle and the penile artery, thereby inducing penile erection. Accordingly, generation of NO is critical to sustain penile erection. Therefore, a combined use of L-arginine, which is the substrate of nitric oxide synthase, and a substance which facilitates generation of NO in blood vessels will be greatly advantageous in triggering sufficient release of NO in the corpus cavernosum, thereby inducing relaxation of the smooth muscle, consistent inflow of blood and treatment of erectile dysfunction.

In an aspect of the present disclosure, a composition comprising the ginseng berry extract as an active ingredient includes a pharmaceutical composition or a food composition. In another aspect of the present disclosure, the composition comprising the ginseng berry extract as an active ingredient includes a pharmaceutical additive composition or a food additive composition.

The pharmaceutical composition comprising the ginseng berry extract as an active ingredient according to the present disclosure may be prepared into solid, semisolid or liquid form for oral or parenteral administration, by adding a commonly used inorganic or organic carrier.

Preparation forms for oral administration may include tablet, pill, granule, soft and hard capsule, powder, fine granule, dust, emulsion, syrup, pellet, and the like. Preparation forms for parenteral administration may include injection, drop, ointment, lotion, spray, suspension, emulsion, suppository, and the like. The composition according to the present disclosure may be prepared easily by a method commonly used in the art. Surfactant, excipient, colorant, fragrance, preservative, stabilizer, buffer, suspending agent, or other adjuvants may be used adequately.

The active ingredient included in the composition according to an aspect of the present disclosure may be mixed with a carrier or encapsulated in a receptacle-type carrier. In case a diluent is used as carrier, the diluent may be a solid, semisolid or liquid substance that can act as carrier, excipient or medium for the active ingredient. Examples of adequate carrier, excipient or diluent include lactose, dextrose, sucrose, sorbitol, mannitol, calcium silicate, cellulose, methyl cellulose, microcrystalline cellulose, polyvinylpyrrolidone, water, methyl hydroxybenzoate, propyl hydroxybenzoate, talc, magnesium stearate or mineral oil. In another aspect of the present disclosure, the composition may further include filler, antiflocculant, lubricant, humectant, fragrance, emulsifier, antiseptic, or the like.

The pharmaceutical composition according to an aspect of the present disclosure may be formulated by a method well known in the art so that the active ingredient can be released in an immediate, sustained or controlled manner after being administered to a mammal.

The pharmaceutical composition according to an aspect of the present disclosure may be administered through various routes, including orally, intradermally, subcutaneously, intravenously, intraperitoneally, intramuscularly, topically using patch, or iontophoretically, although not being limited thereto. In another aspect of the present disclosure, the pharmaceutical composition may be topically applied or orally administered.

For human, a daily dosage of the active ingredient may be 1-100 mg/kg body weight, specifically 5-70 mg/kg body weight. Administration may be made once or several times a day. However, the actual dosage of the active ingredient may be determined considering various factors, including particular disease to be treated, administration route, age, sex and body weight of the patient, severity of the disease, and the like. Accordingly, the afore-mentioned administration dosage by no means limits the scope of the present disclosure.

The food composition comprising the ginseng berry extract as an active ingredient according to the present disclosure includes a food additive composition or a health food composition and may be prepared into tablet, hard capsule, soft capsule, pill, granule, drink, diet bar, chocolate, caramel, confectionery and the like by adding ingredients commonly used in the related art. Further, functional ingredients suitable for a health food composition may be added adequately.

EXAMPLES

The following examples illustrate the present disclosure in more detail, but are not intended to limit the scope of the present disclosure.

[Example 1] Preparation of Ginseng Berry Extract

1) Pre-treatment of ginseng berry: Seeds were separated and removed from harvested raw ginseng berry. Pulp and pericarp of ginseng berry were dried using sunlight or hot air to obtain dried ginseng berry.

2) Preparation of ginseng berry extract: After adding 3 L of ethanol to 1 kg of the dried ginseng berry, 300 g of ginseng berry extract was obtained by extraction under reflux, followed by filtration and concentration under reduced pressure at 40-45° C.

[Example 2] Preparation of Ginseng Berry Saponin Concentrate 100 g of the ginseng berry extract obtained in Example 1 was dissolved in 1 L of water. Oil-soluble constituents were removed using a separatory funnel, by adding 500 mL of diethyl ether. Then, 500 mL of water-saturated butanol was added to the remaining water layer. This procedure was repeated 3 times. The resultant butanol layer was concentrated under reduced pressure to obtain 60 g of ginseng berry saponin concentrate.

[Comparative Example 1] Preparation of Ginseng Root Extract

Ginseng root extract was prepared in substantially the same manner as Example 1, except for using red ginseng root instead of ginseng berry.

[Test Example 1] Comparison of Components of Ginseng Berry Extract, Ginseng Berry Saponin Concentrate and Ginseng Root Extract 1. Analysis of Ginsenoside (Ginseng Saponin) Components Ginsenoside (ginseng saponin) components in the ginseng berry extract, the ginseng berry saponin concentrate and the ginseng root extract prepared in Examples 1-2 and Comparative Example 1 were analyzed. The result is given in Table 1 and FIG. 1 (unit: wt %).

TABLE 1

| Ginsenoside components | | Example 1 | Example 2 | Comparative Example 1 |
|---|---|---|---|---|
| PPD (protopanaxadiol) | Rb1 | 1.46 | 2.83 | 4.35 |
| | Rb2 | 3.31 | 6.44 | 1.2 |
| | Rb3 | 0.76 | 1.47 | 0.95 |
| | Rc | 3.77 | 7.34 | 5.05 |
| | Rd | 4.83 | 9.39 | 1.2 |
| PPT (protopanaxatriol) | Re | 17.40 | 33.82 | 1.6 |
| | Rg1 | 1.11 | 2.16 | 2 |
| | Rg2 | 0.78 | 1.52 | 0.35 |
| Total amount of ginsenoside | | 33.42 | 64.97 | 16.70 |
| PPD/PPT ratio | | 0.733 | 0.732 | 3.228 |

As seen from Table 1 and FIG. 1, the saponin composition of the ginseng berry extract and the ginseng root extract was quite different. In particular, the ginseng berry extract had very high contents of Rd and Re as compared to the ginseng root extract. Also, the ratio of PPD (protopanaxadiols; ginsenosides Rb1, Rb2, Rc and Rd) to PPT (protopanaxatriols; ginsenosides Re, Rg1 and Rg2) was distinctly different in the ginseng berry extract and the ginseng root extract. The ginseng berry saponin concentrate of Example 2, which was obtained by concentrating the ginsenosides of the ginseng berry extract of Example 1, contained about 2 times more ginsenosides than Example 1.

2. Analysis of Mineral Component of Ginseng Berry Extract

Assuming that the extract of ginseng berry, which is 'fruit' of ginseng, prepared in Example 1 would include vitamin and mineral components that are hardly included in ginseng root extract, component analysis was carried out. The result is given in Table 2.

TABLE 2

| Components | Contents | Components | Contents |
|---|---|---|---|
| Potassium (mg/100 g) | 5865.57 | Magnesium (mg/100 g) | 354.38 |
| Calcium (mg/100 g) | 819.26 | Zinc (mg/100 g) | 178.49 |
| Iron (mg/100 g) | 59.31 | Vitamin A (µg/100 g, RE) | 213.11 |
| Phosphorus (mg/100 g) | 187.17 | Vitamin B1 (mg/100 g) | 12.29 |
| Vitamin B$_2$ (mg/100 g) | 8.45 | Vitamin B$_6$ (mg/100 g) | 10.50 |
| Vitamin C (mg/100 g) | 4.91 | Vitamin E (mg/100 g, α-TE) | 23.61 |
| Vitamin K (µg/100 g) | 232.12 | Niacin (mg/100 g, NE) | 5.76 |
| Pantothenic acid (mg/100 g) | 5.87 | Folic acid (µg/100 g) | 349.97 |

As seen from above, the ginseng berry extract contains the 16 vitamin and mineral components plentifully, unlike the ginseng root extract. Based on the finding, the following experiments were carried out in order to confirm the effect of the ginseng berry extract on blood vessels, skin beauty and male sexual function.

[Test Example 2] Effect of Ginseng Berry Extract on Nitric Oxide (NO) Generation in Human Umbilical Vein Endothelial Cells (HUVECs)

Endothelial nitric oxide synthase (eNOS) exists in human endothelial cells. Increased eNOS activity results in NO generation, thereby dilating blood vessels and facilitating blood circulation. Human endothelial cells were cultured and treated with the ginseng berry extract (Example 1), the ginseng berry saponin concentrate (Example 2) and the ginseng root extract (Comparative Example 1), and NO generation quantity was compared.

Endothelial cells were adhered on a gelatin-coated 24-well plate, with a density of $2.5 \times 10^4$ cells/well. The cells were cultured for 12 hours using a growth medium. The endothelial cells were pre-treated for 12 hours, using the ginseng berry extract, the ginseng berry saponin concentrate or the ginseng root extract (Examples 1-2 and Comparative Example 1). Then, they, including a non-treated group, were treated with 10 µmol/L DAF-FM diacetate (Molecular Probe, Oreg.) at 37° C. for 30 minutes in an FBS-free M199 medium. Subsequently, the endothelial cells were washed 3 times with an FBS-free M199 medium, put in a parallel plate flow chamber, and stimulated with light isolated from a mercury lamp. Excitation wavelength was 488 nm. Fluorescence of 515 nm is emitted when DAF binds with NO. FIG. 2a shows confocal laser microscopic images (Atto Bioscience, USA) of endothelial cells, and FIG. 2b compares intensity of fluorescence analyzed using Image-Pro Plus v 4.5 software (Media Cybernetics, San Diego, Calif., USA) with that of the non-treated group.

As seen in FIGS. 2a and 2b, the ginseng berry extract of Example 1 according to the present disclosure and the ginseng berry saponin concentrate of Example 2 exhibited 1300-2000% of NO generation at 100 μg/mL, as compared to the non-treated group. In contrast, the ginseng root extract of Comparative Example 1 showed about 100-200% of NO generation at the same concentration of 100 μg/mL. In particular, the ginseng berry saponin concentrate of Example 2 exhibited more NO generation. Accordingly, it was confirmed that ginseng berry extract provides significantly better NO generation effect in endothelial cells than the ginseng root extract. The outstanding NO generation ability of the ginseng berry extract of Example 1 and the ginseng berry saponin concentrate of Example 2 results in dilation of blood vessels and facilitates blood circulation.

[Test Example 3] Viability of Endothelial Cells

The most basic step of preventing aging of blood vessels and facilitating angiogenesis is activating endothelial cells. Improvement of viability of endothelial cells was compared between a positive control group (VEGF; vascular endothelial growth factor) and ginseng berry extract (Example 1)- and ginseng berry saponin concentrate (Example 2)-treated groups.

Viability of the endothelial cells was measured by crystal violet staining. First, the endothelial cells were adhered on a 24-well plate, at $5 \times 10^4$ cells/well, and cultured for 12 hours using a growth medium. Then, after treating for 6 hours with an M199 medium containing 1% serum, thereby equalizing the cell cycle, the cells were treated with the ginseng berry extract of Example 1 or the ginseng berry saponin concentrate of Example 2 at 25, 50 and 100 μg/mL, respectively, or with the positive control substance. After 18-24 hours, the medium was removed and 300 μL of crystal violet stain was added to stain only the living endothelial cells. After leaving at room temperature for about 30 minutes, the cells were washed 2-3 times with phosphate buffered saline (PBS) and lysed with 1% SDS solution. Absorbance at 550 nm was compared between the positive control group and the treatment groups of Examples 1 and 2 to measure the viability of cells.

Figure 3A:
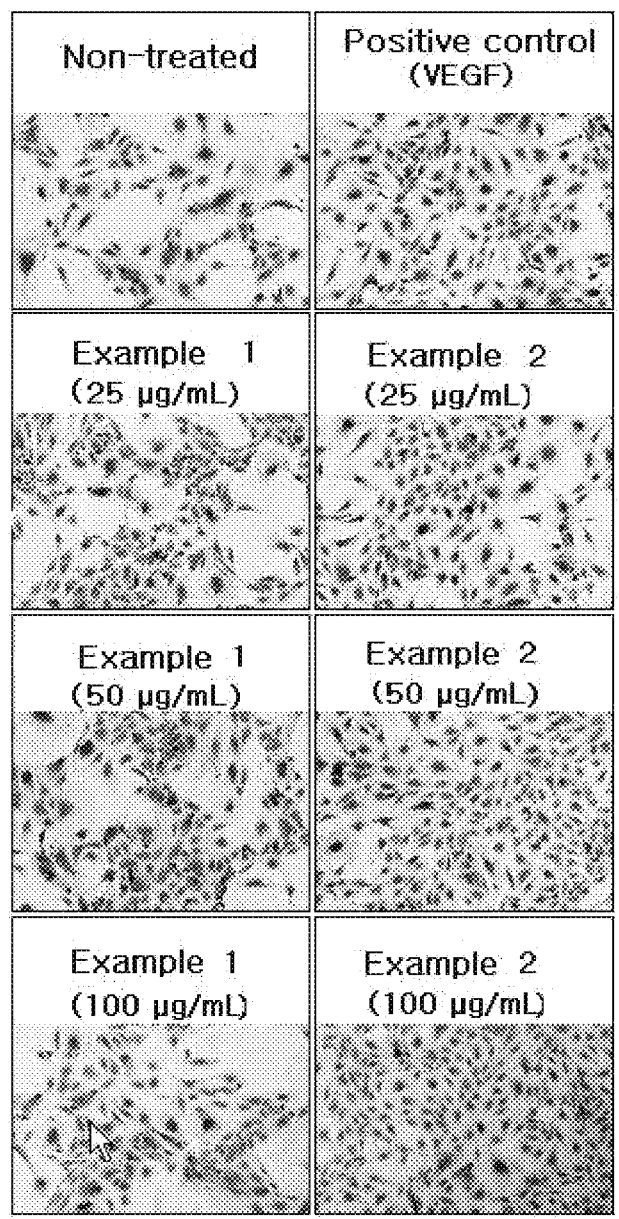
FIG. 3a shows proliferation of surviving endothelial cells, and FIG. 3b compares absorbance of stained endothelial cells.
Figure 3B:
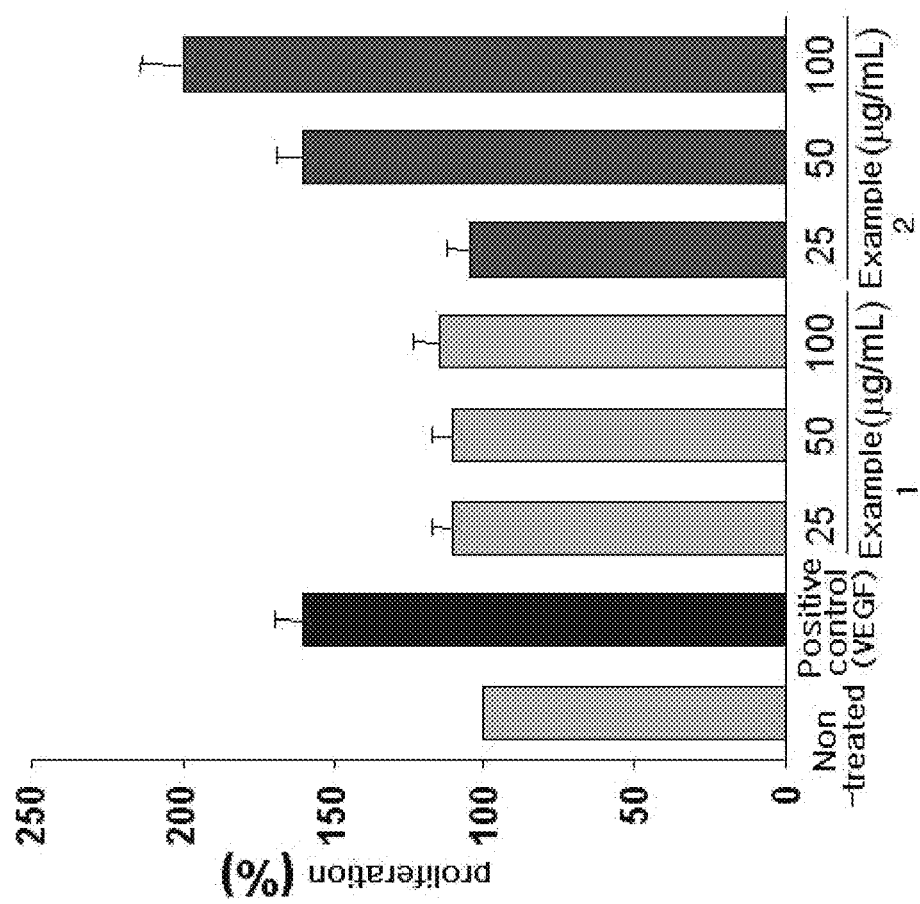

FIG. 3a shows surviving endothelial cells, and FIG. 3b compares absorbance of the stained endothelial cells. As seen in FIG. 3a and FIG. 3b, the ginseng berry extract (Example 1)- and the ginseng berry saponin concentrate (Example 2)-treated groups exhibited better viability of endothelial cells and enhanced cell proliferation than the non-treated group. Especially, Example 2 showed viability of endothelial cells even better than the positive control group (VEGF). Therefore, it was confirmed that the ginseng berry extract improves viability of endothelial cells and facilitate proliferation thereof, thereby preventing aging of blood vessels and facilitating angiogenesis.

[Test Example 4] Improvement of Endothelial Cell Mobility (Migration of HUVECs)

Figure 4A:
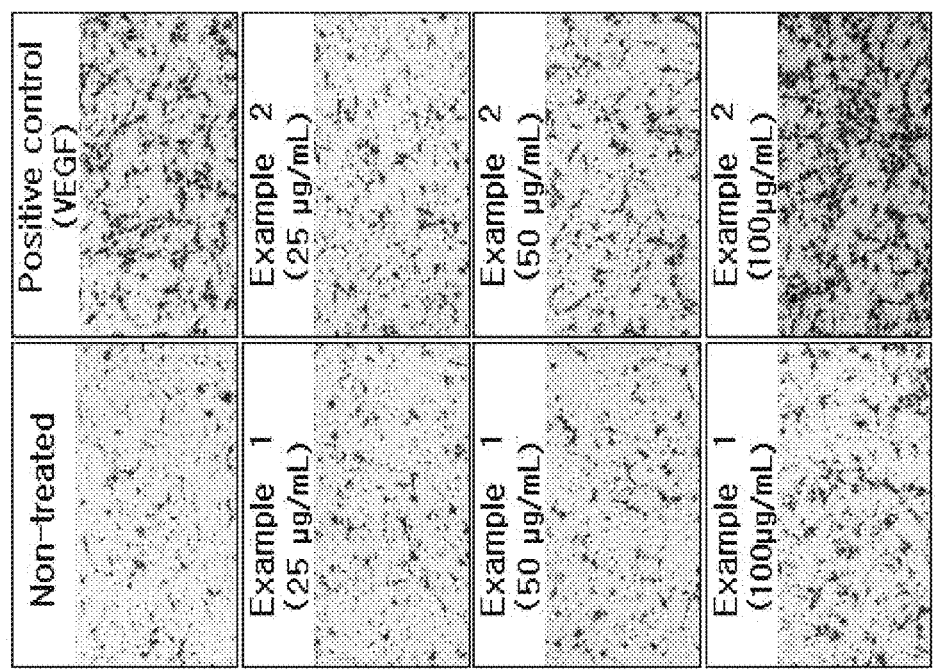
FIG. 4a shows mobility of stained endothelial cells, and FIG. 4b compares mobility of the cells with that of the non-treated group.

Cell mobility was measured and analyzed as a measure of angiogenesis. Cell mobility analysis was carried out using a Boyden's chamber (transwell). 600 μL of serum-free M199 medium was added to a 24-well plate. After treating the medium with the ginseng berry extract or the ginseng berry saponin concentrate (Examples 1 and 2; 25, 50 and 100 μg/mL, respectively) or the positive control substance, gelatin (1 mg/mL) was applied on the lower surface of the transwell and $2 \times 10^4$ cells were adhered on the upper surface. About 4 hours later, the cells on the upper surface were removed using a swab, and the cells that migrated to the lower surface were counted after staining with hematoxylin and eosin. FIG. 4a shows mobility of the stained endothelial cells, and FIG. 4b compares mobility of the cells with that of the non-treated group.

Figure 4B:
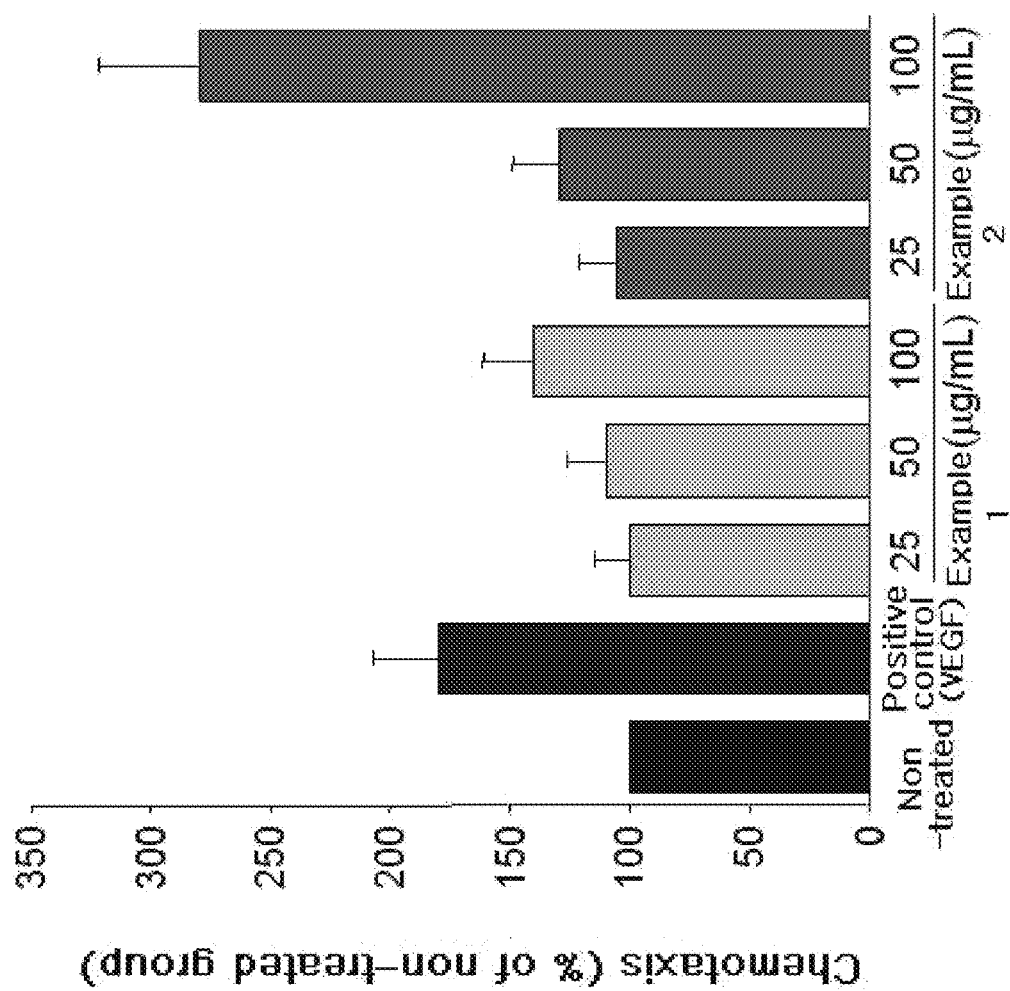

As seen in FIGS. 4a and 4b, Examples 1 and 2 showed the effect of improving the mobility of endothelial cells. Especially, Example 2 showed better effect than the positive control substance VEGF. Accordingly, it can be concluded that the ginseng berry extract improves the mobility of vascular endothelial cells, which is one of key mechanisms in angiogenesis.

[Test Example 5] Facilitation of Tube Formation by Endothelial Cells

Figure 5A:
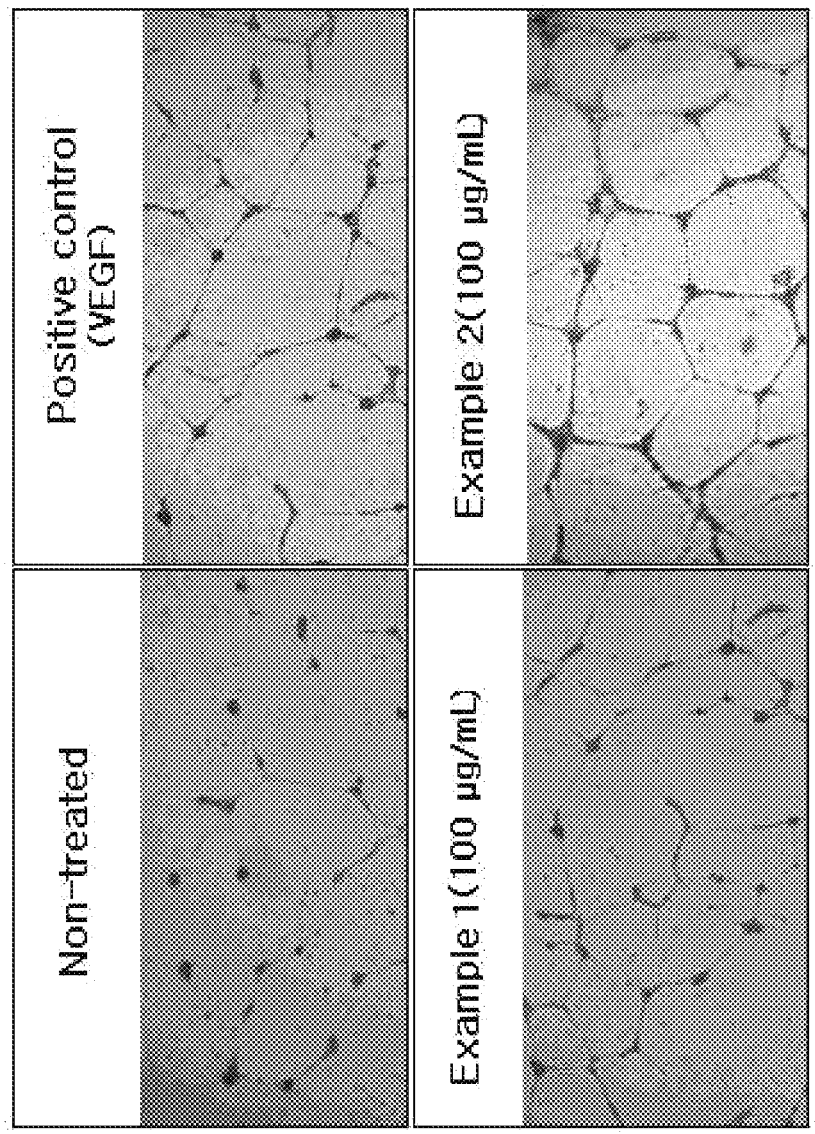
FIG. 5a shows fixed, stained endothelial cells, and FIG. 5b compares tube length with that of non-treated group.

As a measure of angiogenesis control ability, the degree of tube formation by cells was measured. In general, the ability of tube formation by cells is tested using Matrigel. 250 μL of Matrigel was coated on a 24-well plate and $2.5 \times 10^4$ cells were adhered on the Matrigel. With predetermined time intervals, tube formation was observed for the non-treated group, the positive control group (VEGF) and the ginseng berry extract (Example 1)- and the ginseng berry saponin concentrate (Example 2)-treated groups. At proper time, cells were fixed and stained and the degree of tube formation was analyzed using a computer program. FIG. 5a shows the images of the fixed and stained cells, and FIG. 5b compares tube length with that of the non-treated group.

Figure 5B:
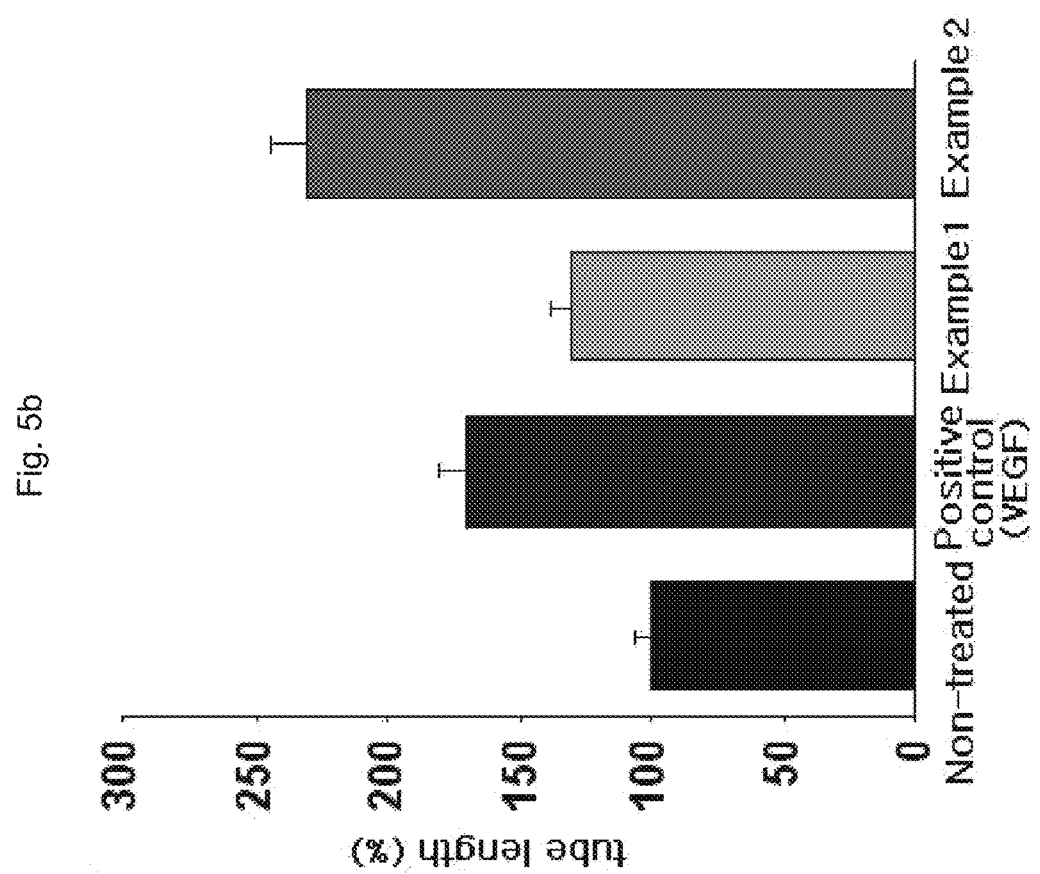

As seen in FIGS. 5a and 5b, Examples 1 and 2 showed the effect of facilitating tube formation, which is one of key mechanisms in angiogenesis. Especially, Example 2 showed better effect than the positive control substance.

[Test Example 6] Facilitation of Vessel Sprouting

Figure 6A:
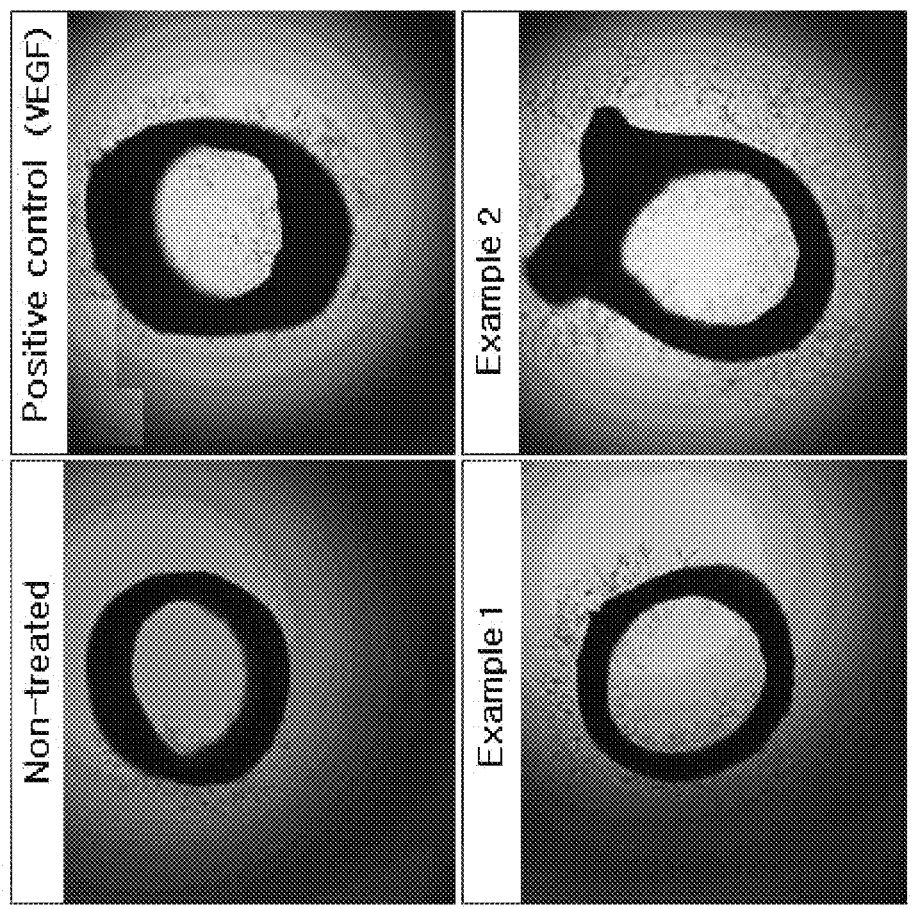
FIG. 6a shows optical microscopic images showing new capillary vessels extending from the aortic ring.

As a measure of angiogenesis control ability, sprouting of vessels was observed. SD rats were used, and the test groups were divided into a non-treated group, a VEGF-treated group, and ginseng berry extract (Example 1)- and ginseng berry saponin concentrate (Example 2)-treated groups. Aortic rings obtained from the SD rats were stored in a serum-free DMEM medium. The medium in which each of the aortic rings was stored was treated with VEGF, the ginseng berry extract (Example 1) or the ginseng berry saponin concentrate (Example 2). While culturing at 37° C. for about 7 days, sprouting of blood vessels was observed. FIG. 6a shows optical microscopic images showing new capillary vessels extending from the aortic ring, and FIG. 6b shows vessel sprouting promoting effect evaluated by measuring length and number of newly formed vessels.

As seen in FIGS. 6a and 6b, the ginseng berry extract (Example 1) and the ginseng berry saponin concentrate (Example 2) showed the effect of facilitating vessel sprouting. Especially, Example 2 showed better effect than the positive control substance. This indicates that the ginseng berry extract has a superior effect of facilitating angiogenesis.

[Test Example 7] Facilitation of Angiogenesis

Figure 7A:
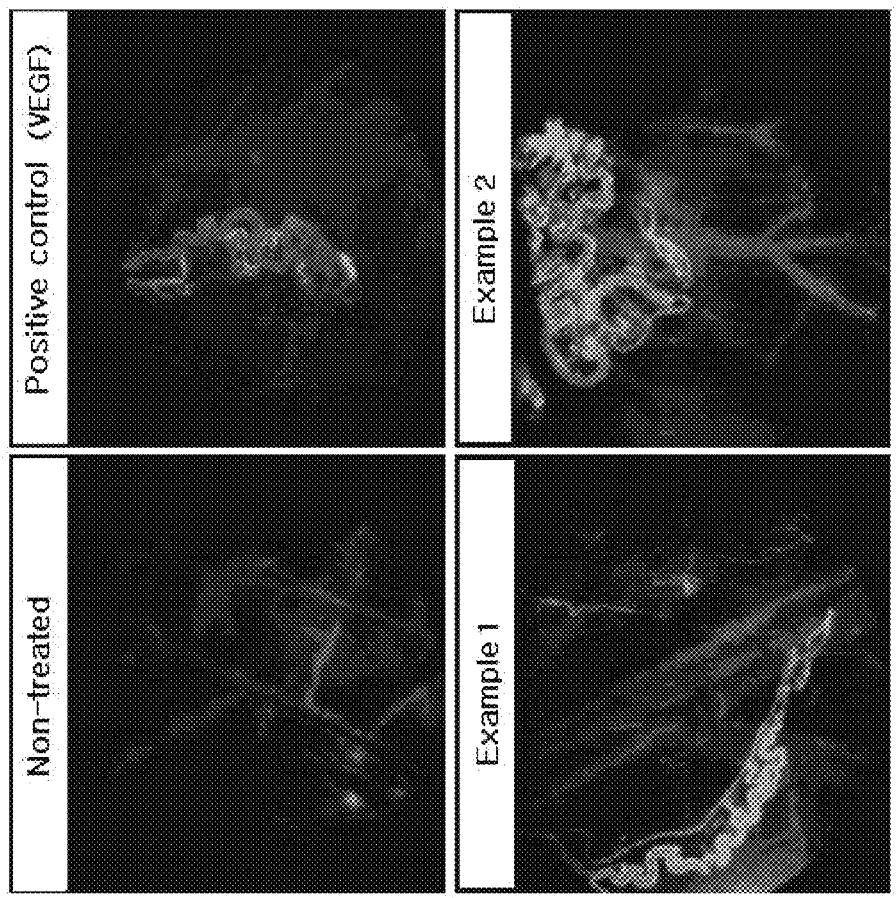
FIG. 7a shows real-time, intravital fluorescence microscopic images of angiogenesis in a mouse.

About 6 to 8 weeks-old male BALB/c mouse was anesthetized using 1.5% isoflurane solution and $O_2/N_2O$. At the abdomen of the mouse, a titanium window chamber (diameter=19 mm, inner diameter=14 mm, thickness=0.7 mm) was implanted. Each of 20 ng of VEGF as control, and the ginseng berry extract (Example 1) and the ginseng berry saponin concentrate (Example 2) was mixed with Matrigel and placed in the tissue inside the window. The cover slip was covered and fixed with a snap ring. Angiogenesis was observed in real time through intravital fluorescence microscopy. 4 days later, 50 µL of dextran (MW 250,000, Sigma Chemical, St. Louis, Mo.) labeled with fluorescein isothiocyanate (FITC) was injected into the tail vein at a concentration of 25 mg/mL, in order to confirm the degree of angiogenesis. FIG. 7a shows real-time, intravital fluorescence microscopic images (Zeiss Axiovert 200M microscopy, Oberkocchen, Germany) taken with an electron-multiplying CCD camera (Photon Max 512; Princeton Instruments, Trenton, N.J.) using blue light (excitation at 440-475 nm, emission at 530-550 nm), and FIG. 7b shows blood vessel change analyzed using the computer program MetaMorph (Universal Imaging Corp., Downingtown, Pa.) (0: fewest changes, 5: most changes).

As seen in FIGS. 7a and 7b the ginseng berry extract (Example 1) and the ginseng berry saponin concentrate (Example 2) showed angiogenic effect in the animal. Especially, Example 2 showed better angiogenic effect than the positive control substance. Accordingly, it was confirmed that the ginseng berry extract is effective in facilitating angiogenesis and, thus, is effective in treating ischemic cardiovascular disease, improving local blood circulation and treating chronic vascular inflammation.

[Test Example 8] Control of Vascular Inflammation

1. Effect of Inhibiting LPS-Induced NO Generation in Macrophages (In Vitro)

Effect of inhibiting LPS-induced NO generation in macrophages was tested in order to confirm the effect of inhibiting vascular inflammation of the ginseng berry extract.

Macrophages (Raw 264.7 cells) were cultured in a medium containing 10% serum under the condition of 5% $CO_2$. After culturing on a 96-well plate incubator to a concentration of $2 \times 10^5$ cells/well and stimulating with LPS (1 µg/mL), the cells were treated with the ginseng berry extract of Example 1 (50 µg/mL and 100 µg/mL), the ginseng berry saponin concentrate of Example 2 (100 µg/mL), the ginseng root extract of Comparative Example 1 (100 µg/mL) or ginsenosides Rg1, Rg2, Rh1 or Re (10 µg/mL and 20 µg/mL), respectively. After keeping the treated cells at 37° C. for 1 hour, the degree of NO generation was measured to compare the effect of inhibiting LPS-induced NO generation of the test substances. NO generation (µM) was measured using the Griess reaction [Minghetti, L. et al., 1991, *Glia* 19. 152-160]. Measurement was made twice and the mean value was calculated. The result is shown in Table 3 and FIG. 8.

TABLE 3

| Sample | Result 1 | Result 2 | Mean ± standard deviation | NO generation relative to negative control (%) |
|---|---|---|---|---|
| Blank | 0.25 | 0.31 | 0.28 ± 0.04 | 1.7 |
| LPS (negative control) | 16.73 | 16.52 | 16.62 ± 0.14 | 100.0 |
| Example 2 (100) | 12.81 | 13.02 | 12.92 ± 0.15 | 77.7 |
| Example 1 (50) | 9.17 | 9.74 | 9.45 ± 0.40 | 56.9 |
| Example 1 (100) | 7.37 | 7.53 | 7.45 ± 0.12 | 44.8 |

TABLE 3-continued

| Sample | Result 1 | Result 2 | Mean ± standard deviation | NO generation relative to negative control (%) |
|---|---|---|---|---|
| Rg1 (10) | 16.38 | 17.27 | 16.83 ± 0.63 | 101.2 |
| Rg1 (20) | 15.75 | 17.25 | 16.50 ± 1.06 | 99.3 |
| Rg2 (10) | 17.00 | 16.36 | 16.68 ± 0.45 | 100.3 |
| Rg2 (20) | 16.18 | 16.19 | 16.19 ± 0.01 | 97.4 |
| Rh1 (10) | 14.92 | 14.81 | 14.86 ± 0.07 | 89.4 |
| Rh1 (20) | 12.29 | 12.66 | 12.48 ± 0.26 | 75.1 |
| Re (10) | 12.92 | 12.02 | 12.47 ± 0.63 | 75.0 |
| Re (20) | 9.85 | 10.59 | 10.22 ± 0.53 | 61.5 |
| Comparative Example 1 (100) | 14.46 | 14.58 | 14.52 ± 0.09 | 87.3 |

As seen from above, the ginseng berry extract according to the present disclosure (Example 1) and the ginseng berry saponin concentrate (Example 2) effectively inhibited generation of NO, and the effect was remarkably superior to that of the ginseng root extract (Comparative Example 1) or the ginsenosides. Accordingly, it was confirmed that the ginseng berry extract of Example 1 and the ginseng berry saponin concentrate of Example 2 are effective in alleviating vascular inflammation and treating vascular inflammation-related ischemic disease such as angina through control of inflammatory response.

The ginseng berry extract of Example 1 showed much better effect of inhibiting NO generation than the ginseng berry saponin concentrate of Example 2, which was prepared by concentrating the saponin in the ginseng berry extract about 2 times, and the effect increased with the concentration of the ginseng berry extract. This shows that the effect of the ginseng berry extract of inhibiting NO generation and alleviating vascular inflammation is enhanced by a synergic effect from ingredients other than saponin included in the ginseng berry.

2. Effect of Controlling Vascular Inflammation (In Vivo)

Based on the experimental result in the cell level, the effect of controlling vascular inflammation of the ginseng berry extract was tested in an animal model. Mice were grouped into a non-treated group, an LPS-induced group, a group treated with the ginseng berry extract of Example 1 (50 µg/mL and 100 µg/mL), a group treated with the ginseng berry saponin concentrate of Example 2 (100 µg/mL), a group treated with the ginseng root extract of Comparative Example 1 (100 µg/mL) and groups treated with ginsenosides Rg1, Rg2, Rh1 or Re (10 µg/mL and 20 µg/mL), with 5 mice per each group.

Figure 10:
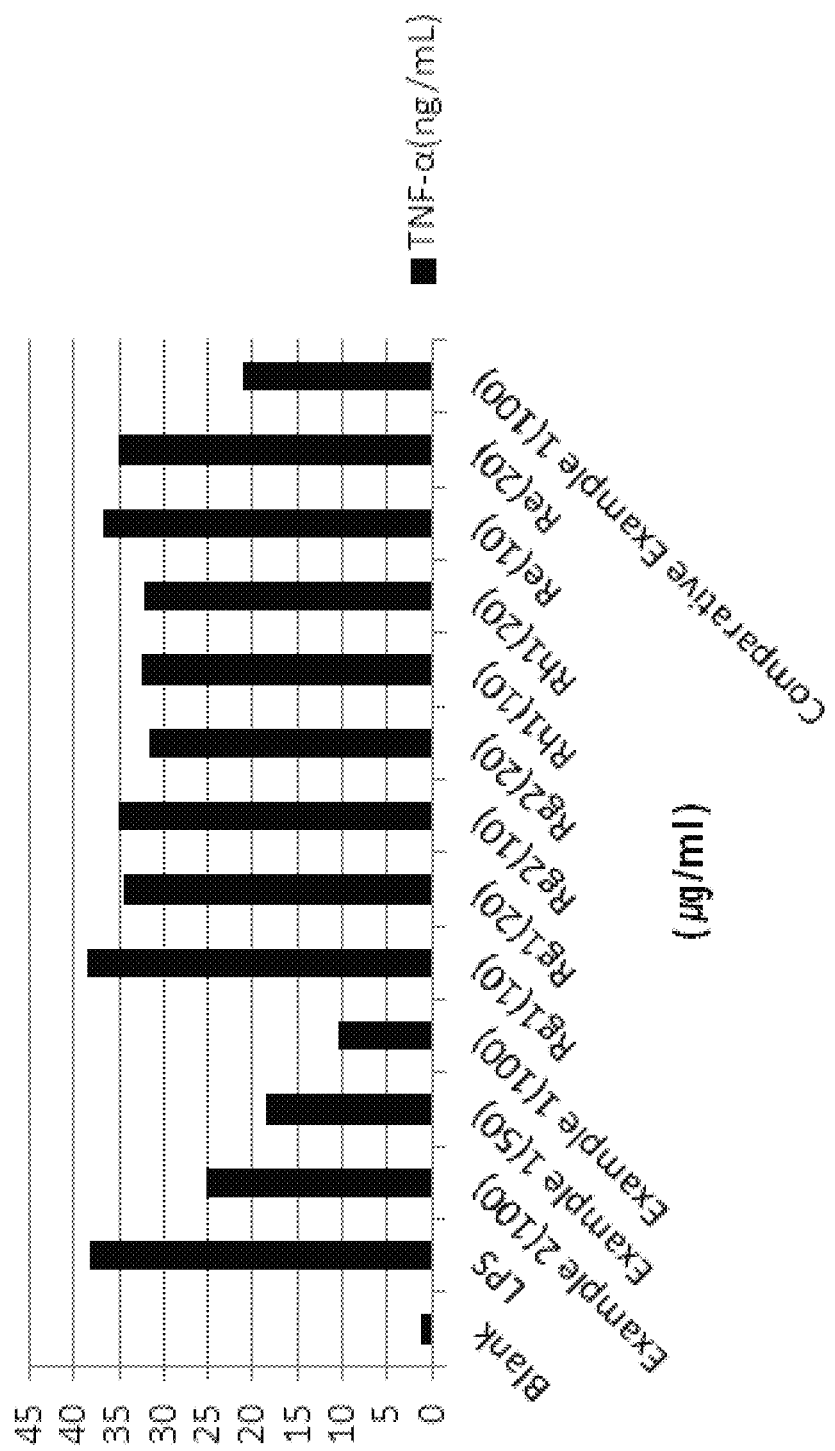
FIG. 10 shows generation of the inflammatory factor TNF-α from mouse blood.
Figure 11:
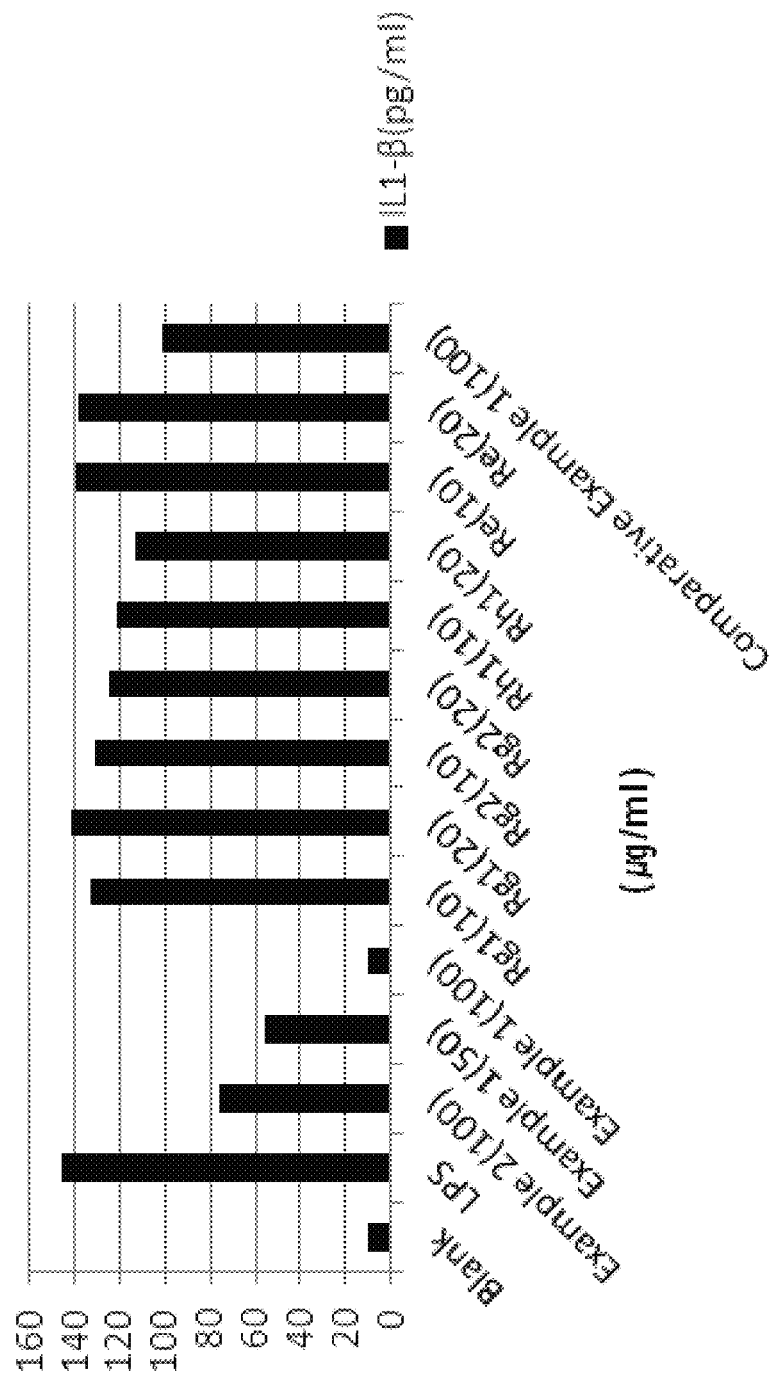
FIG. 11 shows generation of the inflammatory factor IL1-β from mouse blood.

100 mg of each test substance per kg body weight of mouse, diluted in saline solution (0.9% NaCl), was intra-abdominally injected three times from day 1 through day 3. 2 hours after the injection on day 3, LPS diluted in saline solution (1 µg/mL) was injected intra-abdominally at a concentration of about 4 mg per kg body weight of mouse to induce inflammation by inflammatory factors (PGE2, TNF-α and IL1-β). After approximately 12 hours, the abdomen of the mouse was cut open, and blood was taken from the artery of the heart and stored at −40° C. The blood was kept at room temperature for 30 minutes and, after centrifuge at 4° C. and 3,000 rpm for 10 minutes, the supernatant was kept at −20° C. Then, the inflammatory factors PGE2, TNF-α and IL1-β were identified by western blotting. Measurement was made twice and the mean value was calculated. The result is shown in Table 4 and FIG. 9 (PGE2 (ng/mL)), Table 5 and FIG. 10 (TNF-α (ng/mL)), and Table 6 and FIG. 11 (IL1-β (pg/mL)).

TABLE 4

| Sample | Result 1 | Result 2 | Mean ± standard deviation |
|---|---|---|---|
| Blank | 0.4 | 0.42 | 0.41 ± 0.01 |
| LPS (negative control) | 6.2 | 6.41 | 6.31 ± 0.15 |
| Example 2 (100) | 4.55 | 4.5 | 4.53 ± 0.04 |
| Example 1 (50) | 3.9 | 4.01 | 3.96 ± 0.08 |
| Example 1 (100) | 2.11 | 1.99 | 2.05 ± 0.08 |
| Rg1 (10) | 6.29 | 6.35 | 6.32 ± 0.04 |
| Rg1 (20) | 6.31 | 6.21 | 6.26 ± 0.07 |
| Rg2 (10) | 6 | 6.3 | 6.15 ± 0.21 |
| Rg2 (20) | 6.15 | 6.02 | 6.09 ± 0.09 |
| Rh1 (10) | 6.15 | 6.1 | 6.13 ± 0.04 |
| Rh1 (20) | 5.6 | 5.32 | 5.46 ± 0.20 |
| Re (10) | 6.5 | 6.28 | 6.39 ± 0.16 |
| Re (20) | 6.02 | 5.98 | 6.00 ± 0.03 |
| Comparative Example 1 (100) | 5.2 | 5.11 | 5.16 ± 0.06 |

TABLE 5

| Sample | Result 1 | Result 2 | Mean ± standard deviation |
|---|---|---|---|
| Blank | 1.13 | 1.09 | 1.11 ± 0.03 |
| LPS (negative control) | 40.2 | 36.1 | 38.15 ± 2.90 |
| Example 2 (100) | 23.4 | 26.9 | 25.15 ± 2.47 |
| Example 1 (50) | 15.5 | 21.8 | 18.65 ± 4.45 |
| Example 1 (100) | 12.2 | 8.5 | 10.35 ± 2.62 |
| Rg1 (10) | 36.7 | 40.5 | 38.60 ± 2.69 |
| Rg1 (20) | 36.6 | 32.5 | 34.55 ± 2.90 |
| Rg2 (10) | 33.3 | 36.8 | 35.05 ± 2.47 |
| Rg2 (20) | 30.2 | 33 | 31.60 ± 1.98 |
| Rh1 (10) | 28.9 | 36.2 | 32.55 ± 5.16 |
| Rh1 (20) | 29.8 | 34.5 | 32.15 ± 3.32 |
| Re (10) | 39.5 | 34 | 36.75 ± 3.89 |
| Re (20) | 31.8 | 38.5 | 35.15 ± 4.74 |
| Comparative Example 1 (100) | 18.5 | 24 | 21.25 ± 3.89 |

TABLE 6

| Sample | Result 1 | Result 2 | Mean ± standard deviation |
|---|---|---|---|
| Blank | 8.7 | 10.8 | 9.75 ± 1.48 |
| LPS (negative control) | 141 | 152 | 146.50 ± 7.78 |
| Example 2 (100) | 71 | 80.6 | 75.80 ± 6.79 |
| Example 1 (50) | 52 | 60 | 56.00 ± 5.66 |
| Example 1 (100) | 11.8 | 9.6 | 10.70 ± 1.56 |
| Rg1 (10) | 128 | 139 | 133.50 ± 7.78 |
| Rg1 (20) | 135 | 148 | 141.50 ± 9.19 |
| Rg2 (10) | 129 | 134 | 131.50 ± 3.54 |
| Rg2 (20) | 131 | 119 | 125.00 ± 8.49 |
| Rh1 (10) | 116 | 127 | 121.50 ± 7.78 |
| Rh1 (20) | 108 | 117.5 | 112.75 ± 6.72 |
| Re (10) | 131 | 148.5 | 139.75 ± 12.37 |
| Re (20) | 148.2 | 128.4 | 138.30 ± 14.00 |
| Comparative Example 1 (100) | 111.5 | 90.8 | 101.15 ± 14.64 |

As seen from above, the ginseng berry extract of Example 1 and the ginseng berry saponin concentrate ginseng berry extract of Example 2 showed remarkably better effect of inhibiting LPS-induced generation of inflammatory factors as compared to the ginseng root extract (Comparative Example 1) or the ginsenosides. Especially, Example 1 showed better effect. This indicates that ginseng berry extract is effective in inhibiting vascular inflammation and, thereby, controlling vascular inflammation in ischemic disease. Especially, the ginseng berry extract of Example 1 showed much better effect of inhibiting the generation of inflammatory factors than the ginseng berry saponin concentrate of Example 2, and the effect increased with the concentration of the ginseng berry extract. This supports that the effect of the ginseng berry extract of inhibiting vascular inflammation and controlling vascular inflammation in ischemic disease is enhanced by a synergic effect from saponin and other ingredients included in the ginseng berry.

[Test Example 9] Inhibition of Skin Aging and Improvement of Wrinkles

1) Antioxidative Effect

Figure 12:
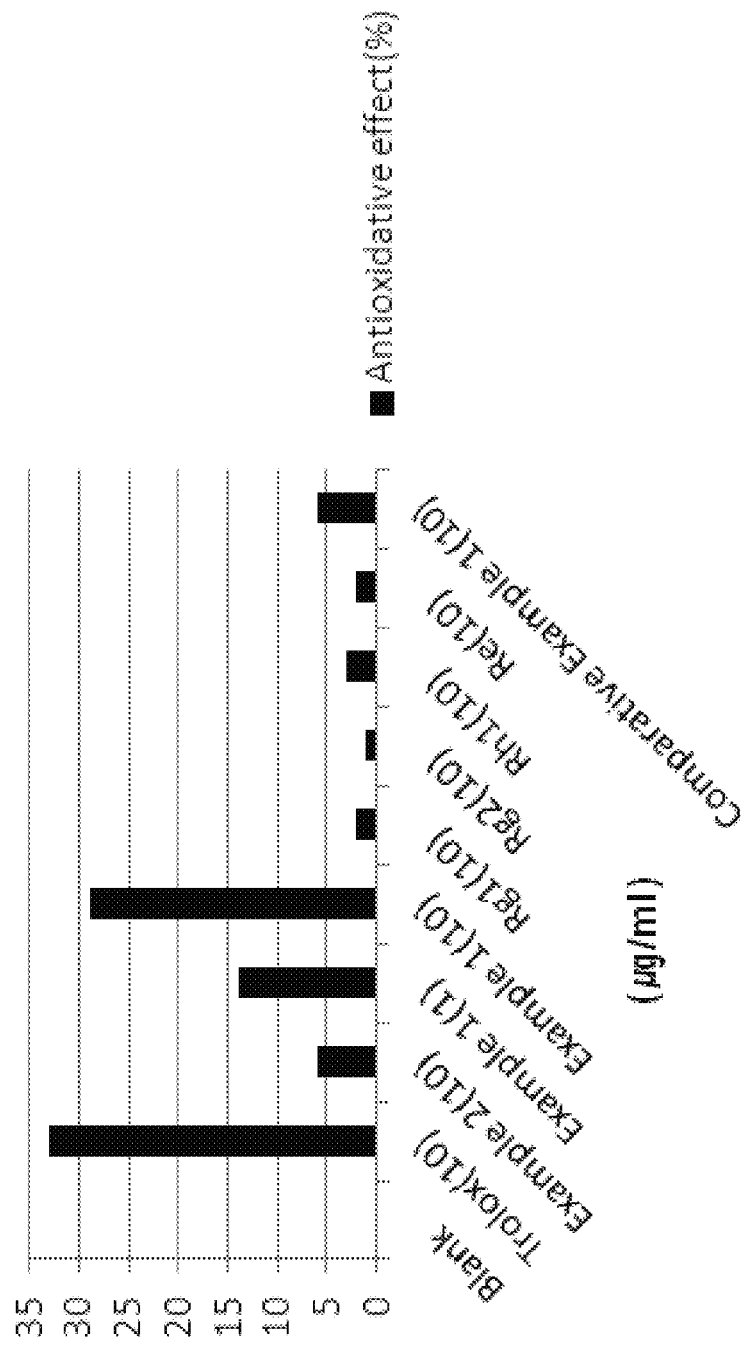
FIG. 12 shows radical oxygen species scavenging effect of test substances.

Antioxidative effect of the ginseng berry extract was investigated by comparing the ability of removing reactive oxygen species (ROS) generated in human HaCaT keratinocytes by ultraviolet (UV) radiation. The ginseng berry extract of Example 1 (1 μg/mL and 10 μg/mL), the ginseng berry saponin concentrate of Example 2 (10 μg/mL), the ginseng root extract of Comparative Example 1 (10 μg/mL) and ginsenosides Rg1, Rg2, Rh1 or Re (10 μg/mL) were used as test substances, and Trolox, which is known to have superior antioxidative effect, was used as a positive control substance. The result is shown in Table 7 and FIG. 12.

TABLE 7

| Sample | Antioxidative effect (%) (±standard deviation) |
|---|---|
| Blank | 0 (±1.5) |
| Trolox (10) | 33 (±6) |
| Example 2 (10) | 6 (±3) |
| Example 1 (1) | 14 (±5) |
| Example 1 (10) | 29 (±4) |
| Rg1 (10) | 2 (±1.5) |
| Rg2 (10) | 1 (±1.5) |
| Rh1 (10) | 3 (±1) |
| Re (10) | 2 (±1) |
| Comparative Example 1 (10) | 6 (±4) |

As seen from above, the ginseng berry extract of Example 1 significantly scavenged ROS generated by UV radiation in human HaCaT keratinocytes, as compared to the control group. Especially, the ROS scavenging effect of 10 μg/mL ginseng berry extract was excellent and comparable to that of Trolox, which is used as antioxidative activity index, as compared to the individual ginsenosides, the ginseng root extract and the ginseng berry saponin concentrate. This supports that the effect of the ginseng berry extract of scavenging ROS is enhanced by a synergic effect from saponin and other ingredients included in the ginseng berry. Accordingly, it was confirmed that the ginseng berry extract of the present disclosure (Example 1) significantly scavenges ROS, which is a cause of skin aging, and, thus, is effective in preventing wrinkles, decrease of skin elasticity, pigmentation, and the like.

2) Type I Procollagen Assay

Human fibroblasts were cultured on a 12-well plate incubator to a concentration of $10^5$ cells/well. Then, the medium was replaced by one including the ginseng berry extract of Example 1 (1 μg/mL and 10 μg/mL), the ginseng berry saponin concentrate of Example 2 (10 μg/mL), the ginseng root extract of Comparative Example 1 (10 μg/mL) or ginsenosides Rg1, Rg2, Rh1 or Re (10 μg/mL). 10 ng/mL transforming growth factor β (TGF-β) was used as a positive control substance.

Figure 13:
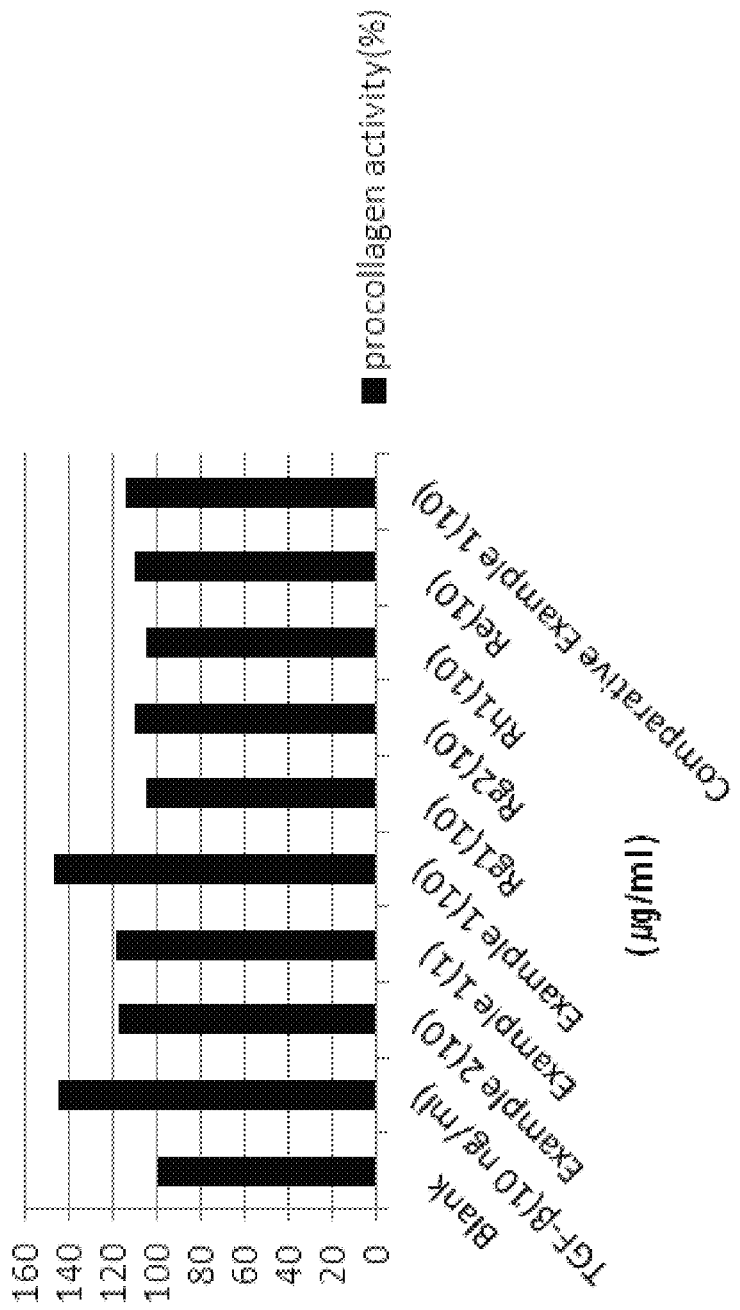
FIG. 13 shows procollagen production after treatment with test substances.

On the 3rd day of culturing, the cells were harvested and the quantity of produced type I procollagen was analyzed using ELISA. The result was calculated as a relative value with respect to the negative control group, which was not treated with a test substance. The result is shown in Table 8 and FIG. 13.

TABLE 8

| Sample | Procollagen activity relative to negative control (%) (±standard deviation) |
|---|---|
| Negative control | 100 (±8) |
| TGF-β (10 ng/mL) | 145 (±10) |
| Example 2 (10) | 118 (±8) |
| Example 1 (1) | 119 (±6) |
| Example 1 (10) | 147 (±10) |
| Rg1 (10) | 105 (±5) |
| Rg2 (10) | 110 (±4) |
| Rh1 (10) | 105 (±4) |
| Re (10) | 110 (±6) |
| Comparative Example 1 (10) | 115 (±3) |

As seen from above, in the normal human fibroblast monolayer culture system, the ginseng berry extract of Example 1 showed a distinct effect of facilitating type I procollagen generation as compared to the control group. This superior effect was not observed from the individual ginsenosides, the ginseng root extract and the ginseng berry saponin concentrate. This supports that the effect of the ginseng berry extract of facilitating procollagen generation is enhanced by a synergic effect from saponin and other ingredients included in the ginseng berry. Accordingly, it was confirmed that the ginseng berry extract of the present disclosure (Example 1) can inhibit the reduction of collagen generation due to aging of human skin and can improve wrinkles.

3) Inhibition of MMP-1 Expression

Figure 14:
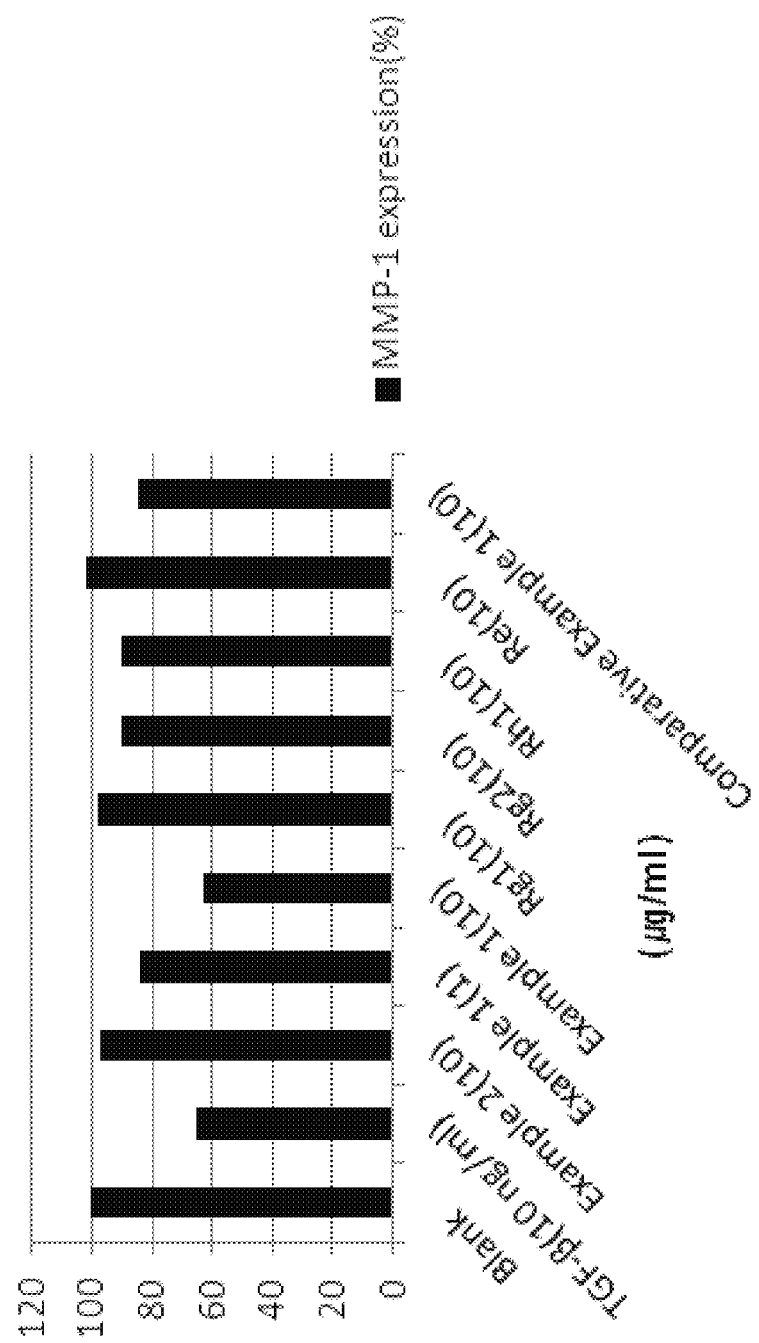
FIG. 14 shows MMP-1 expression inhibiting effect of test substances.

Human fibroblasts were cultured on a 12-well plate incubator to a concentration of $10^5$ cells/well. Then, after irradiating UVB at 40 mJ/cm², the medium was replaced by one including the ginseng berry extract of Example 1 (1 μg/mL and 10 μg/mL), the ginseng berry saponin concentrate of Example 2 (10 μg/mL), the ginseng root extract of Comparative Example 1 (10 μg/mL) or ginsenosides Rg1, Rg2, Rh1 or Re (10 μg/mL). 10 ng/mL TGF-β was used as a positive control substance. On the 2nd day of culturing, the cells were harvested and the quantity of produced matrix metalloproteinase I (MMP-1) was analyzed using ELISA. The result was calculated as a relative value with respect to the control group, which was irradiated with UV without treating with a test substance. The result is shown in Table 9 and FIG. 14.

TABLE 9

| Sample | MMP-1 expression (%) (±standard deviation) |
|---|---|
| Negative control | 100 (±8) |
| TGF-β (10 ng/mL) | 65 (±8) |
| Example 2 (10) | 97 (±8) |
| Example 1 (1) | 84 (±6) |
| Example 1 (10) | 63 (±10) |
| Rg1 (10) | 98 (±5) |
| Rg2 (10) | 90 (±4) |
| Rh1 (10) | 90 (±4) |
| Re (10) | 102 (±6) |
| Comparative Example 1 (10) | 85 (±7) |

In the normal human fibroblast monolayer culture system, the ginseng berry extract of Example 1 significantly inhibited the expression of MMP-1 induced by UVB radiation. This superior effect was not observed from the individual ginsenosides, the ginseng root extract and the ginseng berry saponin concentrate. This supports that the superior effect of the ginseng berry extract of inhibiting MMP-1 expression is enhanced by a synergic effect from saponin and other ingredients included in the ginseng berry. Accordingly, it was confirmed that the ginseng berry extract of Example 1, which contains saponin and other ingredients of ginseng berry, can inhibit the biosynthesis of MMP-1, which is the enzyme involved in the breakdown of skin tissue, induced by internal or external aging factors and, thus, is effective in preventing skin aging and improving wrinkles.

4) Inhibition of Biosynthesis of Cyclooxygenase-2 (COX-2) Induced by UV

Figure 15:
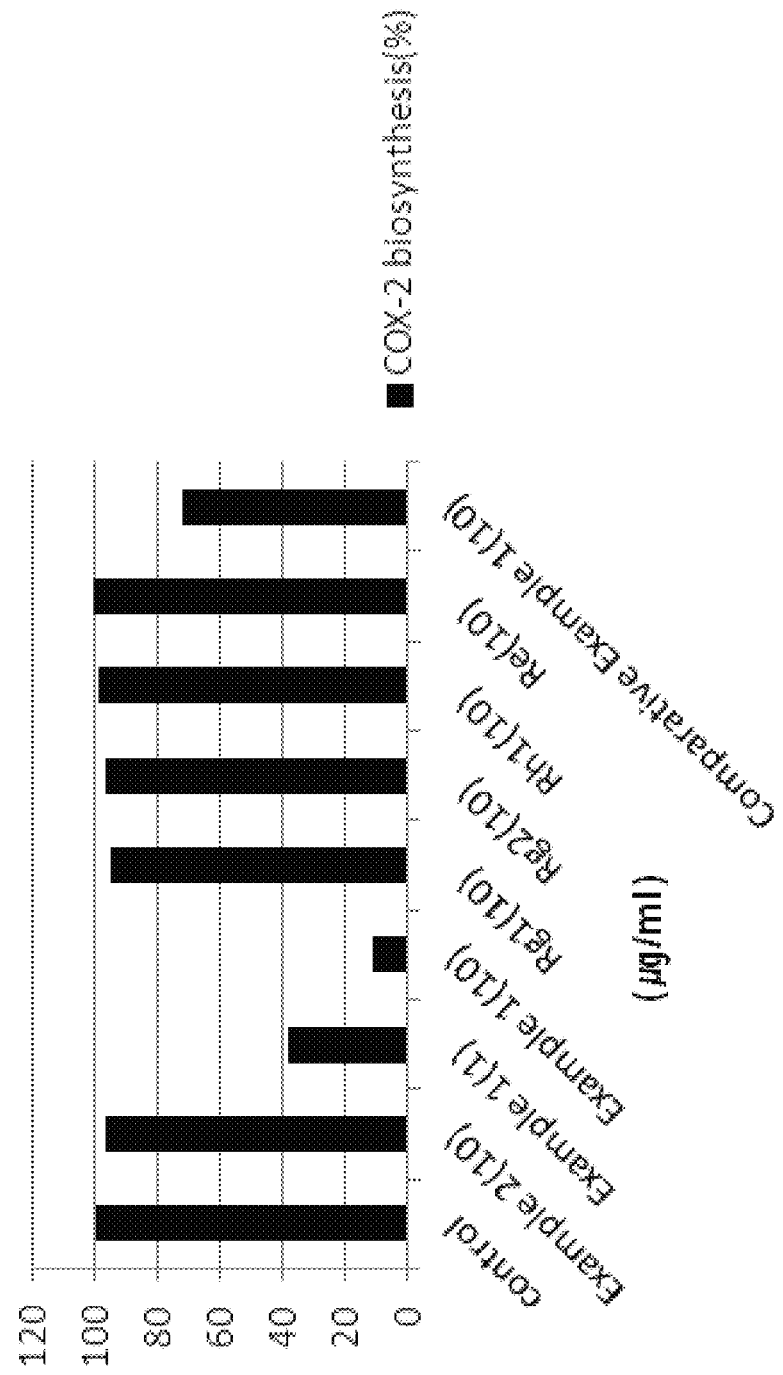
FIG. 15 shows COX-2 biosynthesis inhibiting effect of test substances.

Human fibroblasts were cultured on a 12-well plate incubator to a concentration of $10^5$ cells/well. Then, after irradiating UVA at 15 J/cm², the medium was replaced by one including the ginseng berry extract of Example 1 (0.1 μg/mL, 1 μg/mL and 10 μg/mL), the ginseng berry saponin concentrate of Example 2 (10 μg/mL), the ginseng root extract of Comparative Example 1 (0.1 μg/mL, 1 μg/mL and 10 μg/mL) or ginsenosides Rg1, Rg2, Rh1 or Re (10 μg/mL). On the 2nd day of culturing, the cells were harvested and the quantity of produced COX-2 was analyzed using western blotting. The result was calculated as a relative value with respect to the control group, which was irradiated with UV without treating with a test substance, using a densitometer. The result is given in Table 10 and FIG. 15.

TABLE 10

| Sample | COX-2 biosynthesis (%) (±standard deviation) |
|---|---|
| Negative control | 100 (±4) |
| Example 2 (10) | 97 (±3) |
| Example 1 (0.1) | 63 (±5) |
| Example 1 (1) | 38 (±4) |
| Example 1 (10) | 11 (±5) |
| Rg1 (10) | 95 (±6) |
| Rg2 (10) | 97 (±3) |
| Rh1 (10) | 99 (±3) |
| Re (10) | 101 (±4) |
| Comparative Example 1 (0.1) | 99 (±5) |
| Comparative Example 1 (1) | 91 (±3) |
| Comparative Example 1 (10) | 72 (±4) |

As seen from above, the ginseng berry extract of Example 1 decreased biosynthesis of COX-2 induced by UV in a concentration-dependent manner. This superior effect was not observed from the individual ginsenosides, the ginseng root extract and the ginseng berry saponin concentrate. This supports that the superior effect of the ginseng berry extract of inhibiting COX-2 generation is enhanced by a synergic effect from saponin and other ingredients included in the ginseng berry. Accordingly, it was confirmed that the ginseng berry extract of Example 1, which contains saponin and other ingredients of ginseng berry, can effectively prevent the breakdown of skin tissue by prostaglandin E2 (PGE2) derived from COX-2.

5) Inhibition of Biosynthesis of Tumor Necrosis Factor α (TNF-α) Induced by UV

Figure 16:
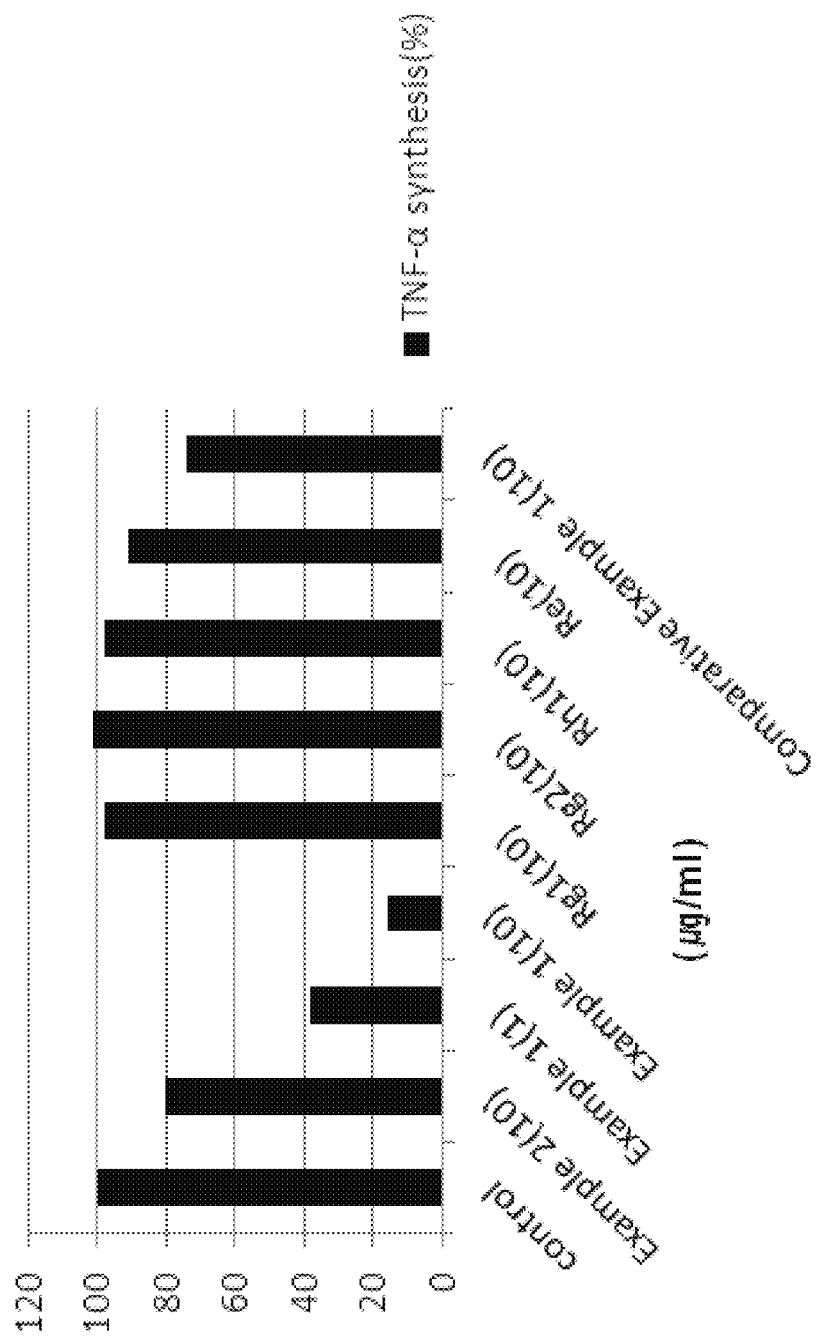
FIG. 16 shows TNF-α biosynthesis inhibiting effect of test substances.

Human keratinocytes were cultured on a 12-well plate incubator to a concentration of $10^5$ cells/well. Then, after irradiating UVB at 30 mJ/cm², the medium was replaced by one including the ginseng berry extract of Example 1 (0.1 μg/mL, 1 μg/mL and 10 μg/mL), the ginseng berry saponin concentrate of Example 2 (10 μg/mL), the ginseng root extract of Comparative Example 1 (0.1 μg/mL, 1 μg/mL and 10 μg/mL) or ginsenosides Rg1, Rg2, Rh1 or Re (10 μg/mL). After 6-24 hours of culturing, the cells were harvested and the quantity of TNF-α was analyzed using ELISA (Pharmingen 555212). The result was calculated as a relative value with respect to the control group, which was irradiated with UV without treating with a test substance. The result is given in Table 11 and FIG. 16.

TABLE 11

| Sample | TNF-α biosynthesis (%) (±standard deviation) |
|---|---|
| Negative control | 100 (±6) |
| Example 2 (10) | 80 (±2) |
| Example 1 (0.1) | 72 (±4) |
| Example 1 (1) | 38 (±6) |
| Example 1 (10) | 16 (±4) |
| Rg1 (10) | 98 (±5) |
| Rg2 (10) | 101 (±2) |
| Rh1 (10) | 98 (±3) |
| Re (10) | 91 (±6) |
| Comparative Example 1 (0.1) | 92 (±5) |
| Comparative Example 1 (1) | 85 (±3) |
| Comparative Example 1 (10) | 74 (±6) |

As seen from above, the ginseng berry extract of Example 1 decreased biosynthesis of TNF-α induced by UV in a concentration-dependent manner. This superior effect was not observed from the individual ginsenosides, the ginseng root extract and the ginseng berry saponin concentrate. This supports that the superior effect of the ginseng berry extract of inhibiting TNF-α biosynthesis is enhanced by a synergic effect from saponin and other ingredients included in the ginseng berry. Accordingly, it was confirmed that the ginseng berry extract of Example 1, which contains saponin and other ingredients of ginseng berry, can effectively prevent skin aging, which may be caused by the biosynthesis of TNF-α.

6) Inhibition of Skin Aging

Hairless mice were selected as an animal model for evaluating whether the ginseng berry extract has skin aging prevention effect. 6 to 7 weeks-old female mice were grouped, with 10 mice per each group. After 12 weeks of oral administration of 'normal feed (control)', 'normal feed+ginseng berry extract (Example 1)', 'normal feed+ginseng berry saponin concentrate (Example 2)' or 'normal feed+ginseng root extract (Comparative Example 1)', the mice were irradiated with UV.

Figure 17:
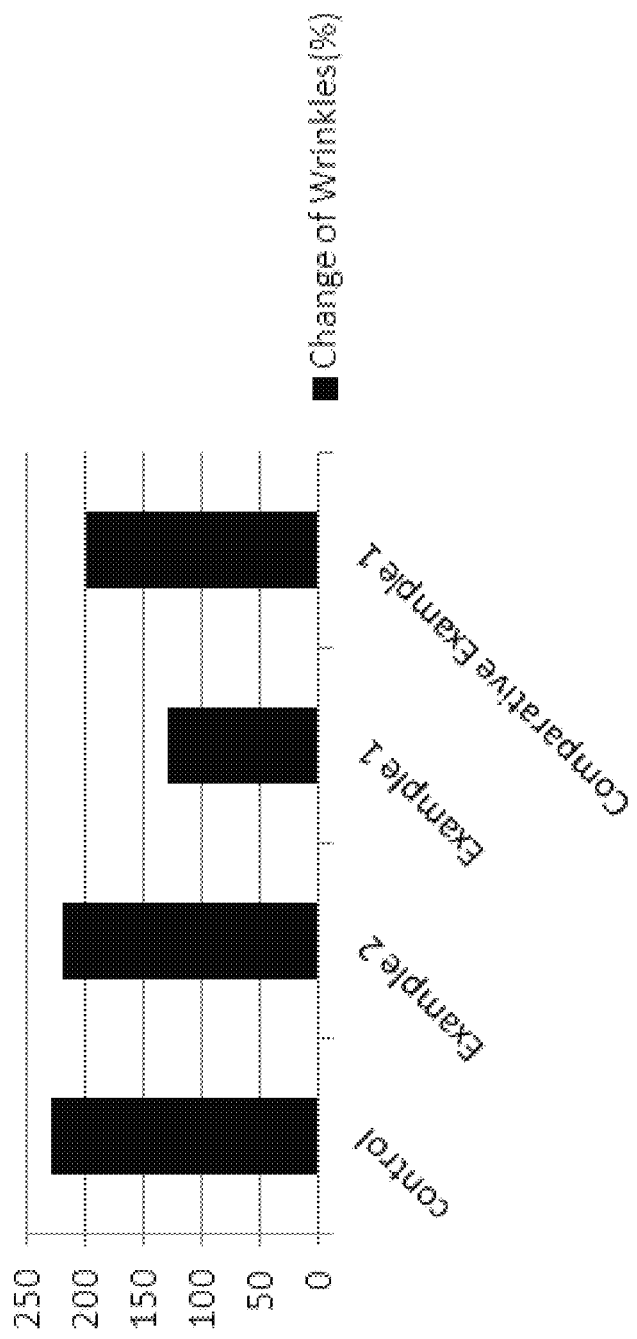
FIG. 17 shows wrinkle formation inhibiting effect of test substances.

Skin wrinkles before and after the UV radiation were compared in the same region using the visiometer system (C+K). Change of skin wrinkles was calculated by the following Equation 1. The result is shown in Table 12 and FIG. 17.

$$\text{Change of wrinkles } (\Delta \%) = \frac{Tdi - Tdo}{Tdo} \times 100 \quad \text{Equation 1}$$

where Tdi is the measurement value on day 90, and Tdo is the measurement value on day 0.

TABLE 12

| Sample | Change of skin wrinkles (%) |
|---|---|
| Control | 230 |
| Example 2 | 220 |
| Example 1 | 130 |
| Comparative Example 1 | 200 |

As seen from above, the test group to which the normal feed and the ginseng berry extract of Example 1 were given showed 130% of skin wrinkle increase, whereas the control group to which the normal feed was given showed 230% of skin wrinkle increase. This superior effect of inhibiting skin wrinkles was not observed from the ginseng root extract and the ginseng berry saponin concentrate. Accordingly, it was confirmed that the ginseng berry extract of Example 1, which contains saponin together with other ingredients of ginseng berry, can effectively prevent skin wrinkle formation and thus can effectively prevent skin aging.

7) Improvement of Wrinkles

Hairless mice were selected as an animal model for evaluating whether the ginseng berry extract provides the effect improving pre-existing wrinkles. 6 to 7 weeks-old female mice were grouped, with 10 mice per each group. After inducing irradiation with UV to induce skin wrinkles, the mice were orally administered with 'normal feed (control)', 'normal feed+ginseng berry extract (Example 1)', 'normal feed+ginseng berry saponin concentrate (Example 2)' or 'normal feed+ginseng root extract (Comparative Example 1)' for 12 weeks.

Figure 18:
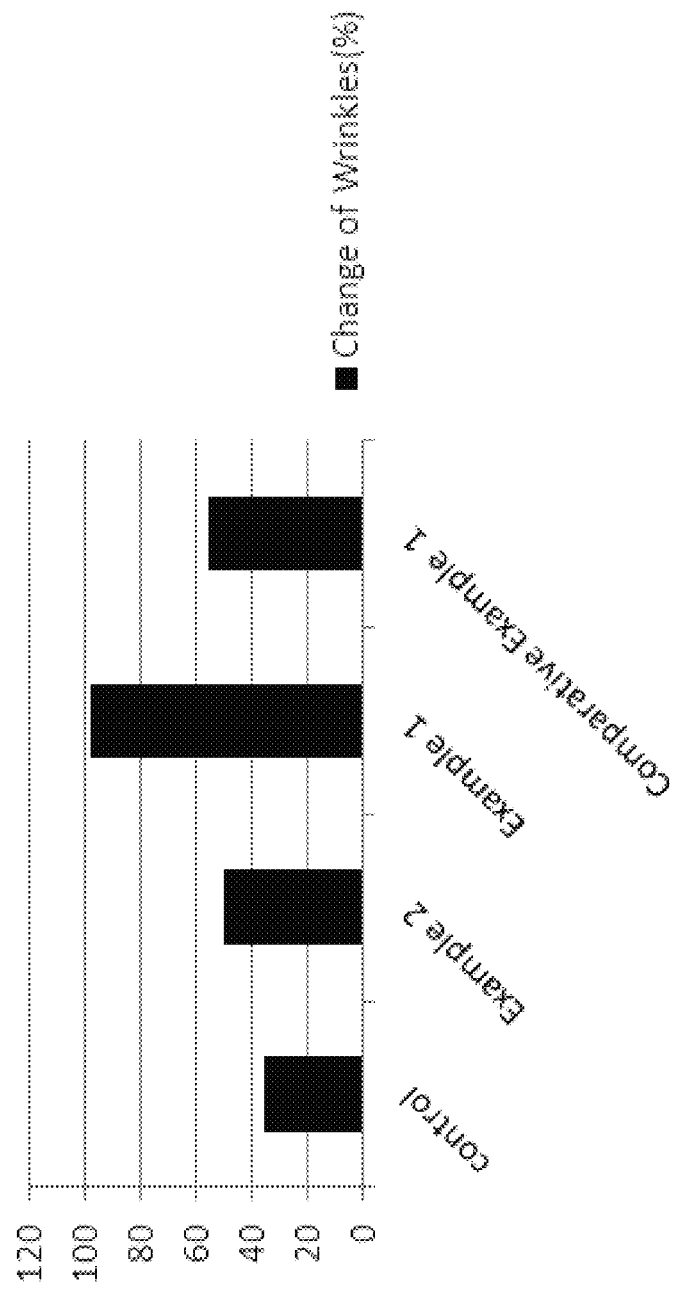
FIG. 18 shows wrinkle improving effect of test substances.

Skin wrinkles before and after the UV radiation were compared in the same region using the visiometer system (C+K). Change of skin wrinkles was calculated by the following Equation 2. The result is shown in Table 13 and FIG. 18.

$$\text{Change of wrinkles } (\Delta \%) = \frac{Tdi - Tdo}{Tdo} \times 100 \quad \text{Equation 2}$$

where Tdi is the measurement value on day 90, and Tdo is the measurement value on day 0.

TABLE 13

| Sample | Change of skin wrinkles (%) (±standard deviation) |
|---|---|
| Control | 35 (±22) |
| Example 2 | 50 (±16) |
| Example 1 | 98 (±17) |
| Comparative Example 1 | 55 (±15) |

As seen from above, the test group to which the normal feed and the ginseng berry extract of Example 1 were given showed 98±17% (mean±standard deviation) of skin wrinkle decrease, whereas the control group to which the normal feed was given showed 35±22% of skin wrinkle decrease. This superior effect of improving pre-existing wrinkles of the ginseng berry extract was not observed from the ginseng root extract and the ginseng berry saponin concentrate. Accordingly, it was confirmed that the ginseng berry extract, which contains saponin together with other ingredients of ginseng berry, can improve skin wrinkle formation and thus can prevent skin aging.

[Test Example 10] Skin Whitening Effect

1) Inhibition of Melanin Generation in Mouse Melanocytes

Inhibition of melanin generation in mouse melanocytes was evaluated in order to confirm the effect of the ginseng berry extract of Example 1 of inhibiting melanin generation.

Figure 19:
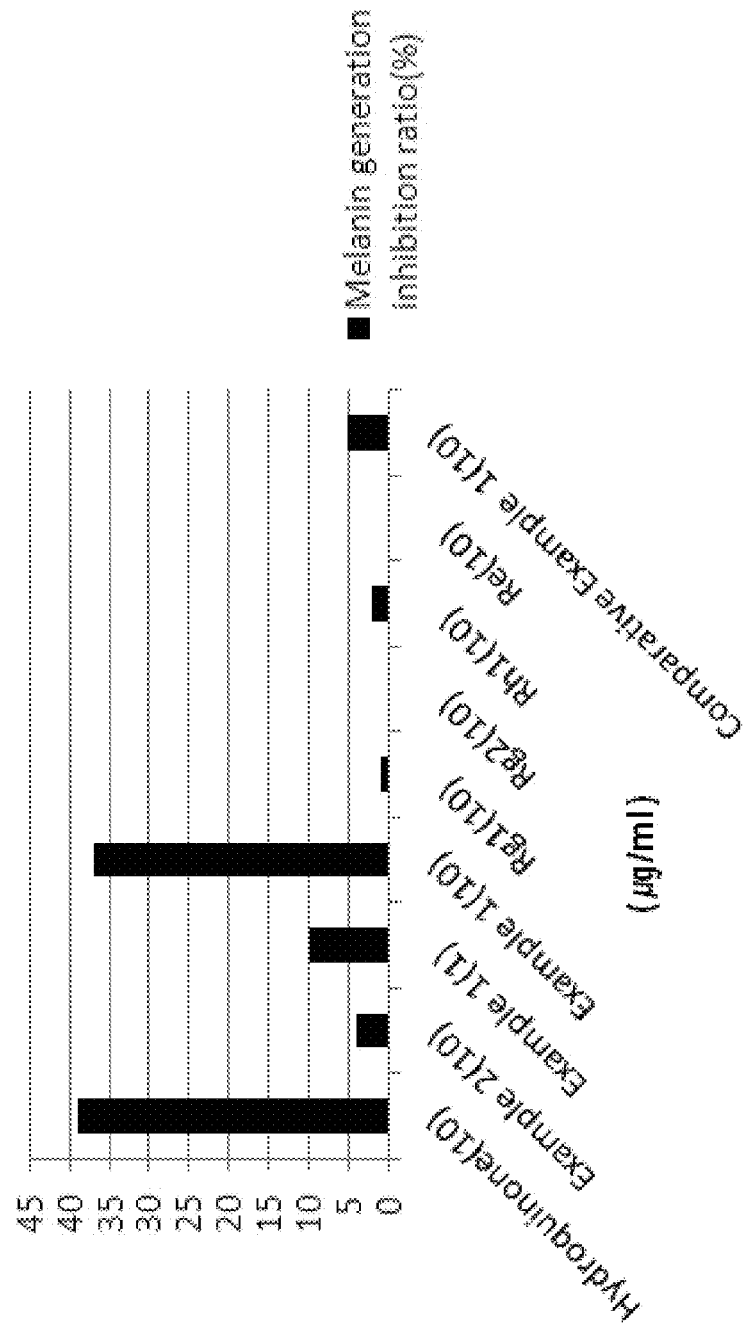
FIG. 19 shows melanin generation inhibiting effect of test substances.

First, melanocytes (MeI-Ab cells) derived from C57BL/6 mouse [Dooley, T. P. et al, *Skin Pharmacol.*, 7, pp. 188-200] were cultured in Dulbecco's modified Eagle's medium (DMEM) containing 10% FBS, 100 nM 2-O-tetradecanoyl-phorbol-13-acetate and 1 nM cholera toxin under the condition of 37° C., 5% $CO_2$. The cultured MeI-Ab cells were separated using 0.25% trypsin-EDTA, and cultured on a 24-well plate to a concentration of $10^5$ cells/well. Starting from day 2, the ginseng berry extract of Example 1 (1 µg/mL, 10 µg/mL and 100 µg/mL), the ginseng berry saponin concentrate of Example 2 (10 µg/mL), the ginseng root extract of Comparative Example 1 (10 µg/mL) or ginsenosides Rg1, Rg2, Rh1 or Re (10 µg/mL) was added for 3 consecutive days. Hydroquinone (10 µg/mL) was used as a positive control substance. Then, after removing the medium and washing with PBS, the cells were dissolved with 1 N sodium hydroxide. Absorbance was measured at 400 nm, and melanin generation inhibition ratio was calculated by Equation 3. The result is given in Table 14 and FIG. 19.

$$\text{Melanin generation inhibiton ratio (\%)} = \quad \text{Equation 3}$$
$$100 - \left(\frac{\text{Absorbance of test substance}}{\text{Absorbance of control}} \times 100\right)$$

TABLE 14

| Sample | Melanin generation inhibition ratio (%) |
|---|---|
| Hydroquinone (10) | 39 |
| Example 2 (10) | 4 |
| Example 1 (1) | 10 |
| Example 1 (10) | 37 |
| Example 1 (100) | 69 |
| Rg1 (10) | 1 |
| Rg2 (10) | 0 |
| Rh1 (10) | 2 |
| Re (10) | 0 |
| Comparative Example 1 (10) | 5 |

As seen from above, the ginseng berry extract of Example 1 showed remarkably superior melanin generation inhibiting effect as compared to the individual ginsenosides, the ginseng root extract and the ginseng berry saponin concentrate. Accordingly, it was confirmed that the ginseng berry extract, which contains saponin together with other ingredients of ginseng berry, provides superior skin whitening effect.

2) Skin Whitening Effect Through Oral Administration

Brown guinea pig was selected as an animal model in order to confirm whether the composition of the ginseng berry extract of Example 1 provides skin whitening effect as health functional food. Minimum erythemal doses of animals in all test groups were measured, then UV with the minimum erythemal dose were irradiated to the animals with 3 times, once a day. The animals were grouped, with 10 mice per each group, and were freely allowed to 'normal feed (control)', 'normal feed+ginseng berry extract (Example 1)', 'normal feed+ginseng berry saponin concentrate (Example 2)' or 'normal feed+ginseng root extract (Comparative Example 1)' for 5 weeks. L value (brightness) was measured using a colorimeter 1, 2, 3, 4 and 5 weeks later. Pigmentation was evaluated by comparing the change in L value before and after UV radiation. The result is given in Table 15.

TABLE 15

| UV radiation | Normal feed | Normal feed + ginseng root extract | Normal feed + Example 1 | Normal feed + Example 2 |
|---|---|---|---|---|
| 1 week later | 7.03 ± 0.28 | 6.90 ± 0.48 | 6.92 ± 0.30 | 6.95 ± 0.68 |
| 2 weeks later | 6.61 ± 0.31 | 6.50 ± 0.11 | 6.04 ± 0.18 | 6.60 ± 0.22 |
| 3 weeks later | 6.42 ± 0.26 | 5.91 ± 0.26 | 4.56 ± 0.25 | 6.11 ± 0.36 |
| 4 weeks later | 6.16 ± 0.45 | 5.66 ± 0.11 | 3.44 ± 0.16 | 5.75 ± 0.31 |
| 5 weeks later | 6.01 ± 0.49 | 5.42 ± 0.23 | 2.88 ± 0.15 | 5.55 ± 0.24 |

As seen from above, the test group to which the ginseng berry extract of Example 1 was administered exhibited the fastest decrease of change in L value. This means that, in the group to which the ginseng berry extract of Example 1 was administered, the darkened skin returns to the original skin color faster than the group to which the ginseng berry saponin concentrate of Example 2 or the ginseng root extract of Comparative Example 1 was administered. Accordingly, it was confirmed that the ginseng berry extract, which contains saponin together with other ingredients of ginseng berry, provides superior skin whitening effect for the skin darkened by UV radiation.

[Test Example 11] Skin Moisturizing Effect

1) Facilitation of Hyaluronic Acid Producing Ability

Hyaluronic acid is a link protein which keeps moisture in the intercellular space and is directly related with skin moisturizing effect.

Figure 20:
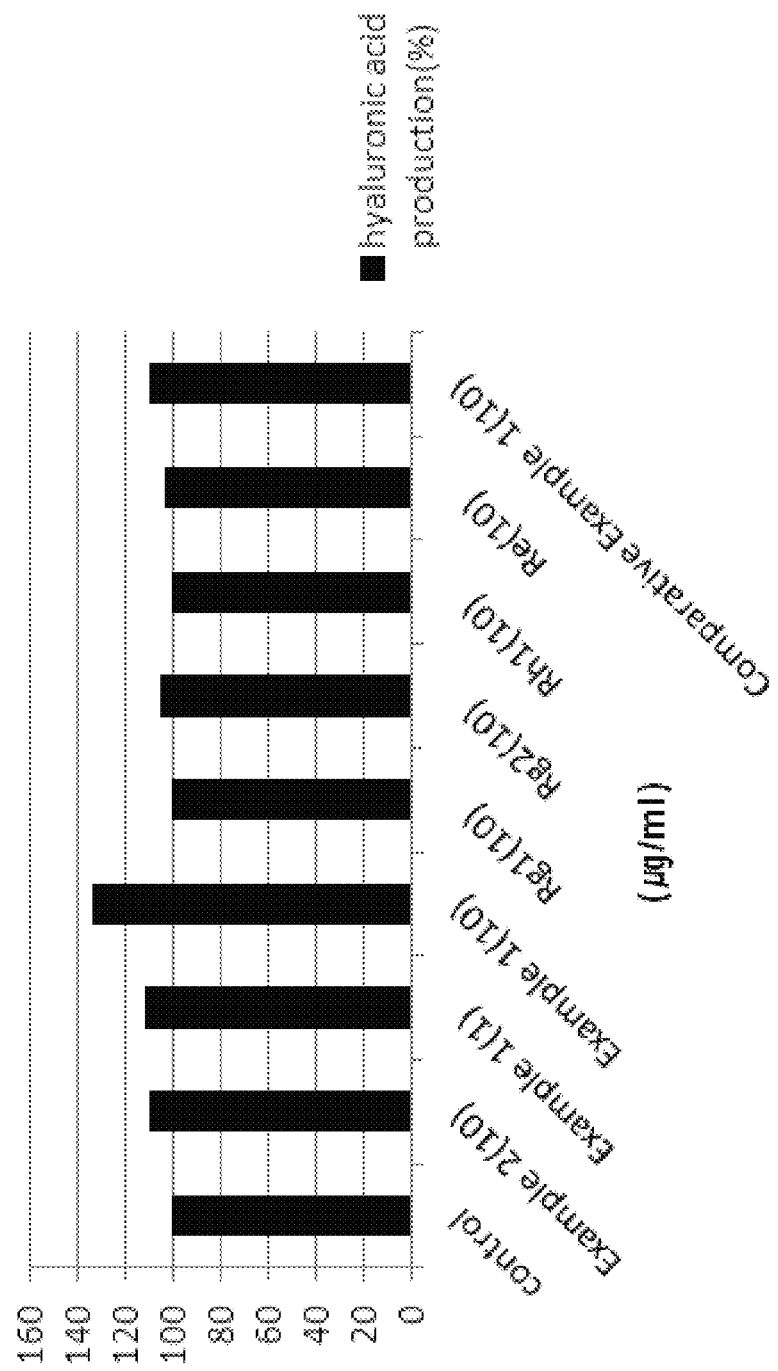
FIG. 20 shows hyaluronic acid generation facilitating effect of test substances.

Human epidermal cells were cultured and the medium was replaced by one containing the ginseng berry extract of Example 1 (1 µg/mL, 10 µg/mL and 100 µg/mL), the ginseng berry saponin concentrate of Example 2 (10 µg/mL), the ginseng root extract of Comparative Example 1 (10 µg/mL) or ginsenosides Rg1, Rg2, Rh1 or Re (10 µg/mL) or a general medium (control). The cells were then cultured for 48 hours under the same conditions. Then, the quantity of hyaluronic acid in the groups was compared using a hyaluronic acid measurement kit. The result is given as relative value with respect to the control group in Table 16 and FIG. 20.

TABLE 16

| Sample | Hyaluronic acid production (%) |
|---|---|
| Control | 100 |
| Example 2 (10) | 110 |
| Example 1 (1) | 112 |
| Example 1 (10) | 134 |
| Example 1 (100) | 189 |
| Rg1 (10) | 100 |
| Rg2 (10) | 105 |
| Rh1 (10) | 100 |
| Re (10) | 103 |
| Comparative Example 1 (10) | 110 |

As seen from above, the ginseng berry extract of Example 1 exhibited the best effect of facilitating the production of hyaluronic acid in the epidermal cells. This means that the ginseng berry extract of Example 1 has excellent hyaluronic acid generation facilitating effect as compared to the ginseng berry saponin concentrate of Example 2 and the ginseng root extract of Comparative Example 1. Accordingly, it was confirmed that the ginseng berry extract of Example 1, which contains saponin and other ingredients of ginseng berry, provides superior moisturizing effect.

2) Skin Moisturizing Effect Through Oral Administration

Hairless mice were selected as an animal model for evaluating whether the ginseng berry extract of Example 1 provides skin moisturizing effect. 6 to 7 weeks-old female mice were grouped, with 10 mice per each group, and 'normal feed (control)', 'normal feed+ginseng berry extract (Example 1)', 'normal feed+ginseng berry saponin concentrate (Example 2) or 'normal feed+ginseng root extract (Comparative Example 1)' was orally administered for 12 weeks. Then, the quantity of hyaluronic acid in the epidermis and the dermis was measured using a hyaluronic acid measurement kit. The result is given in Table 17.

TABLE 17

|  | Normal feed | Normal feed + ginseng root extract | Normal feed + Example 1 | Normal feed + Example 2 |
| --- | --- | --- | --- | --- |
| Hyaluronic acid content (µg/g) | 502.80 ± 16.24 | 539.33 ± 36.11 | 617.89 ± 20.21 | 530.73 ± 46.41 |

As seen from above, the test group to which the ginseng berry extract of Example 1 was administered exhibited increased hyaluronic acid content in the epidermis and the dermis. This remarkable skin moisturizing effect was not observed in the control group to which the normal feed was administered and the group to which the ginseng root extract and the ginseng berry saponin concentrate was administered, respectively. Accordingly, it was confirmed that the ginseng berry extract of Example 1, which contains saponin together with other ingredients of ginseng berry, provides superior moisturizing effect.

[Test Example 12] Increase of NO Generation in Endothelial Cells

Figure 21:
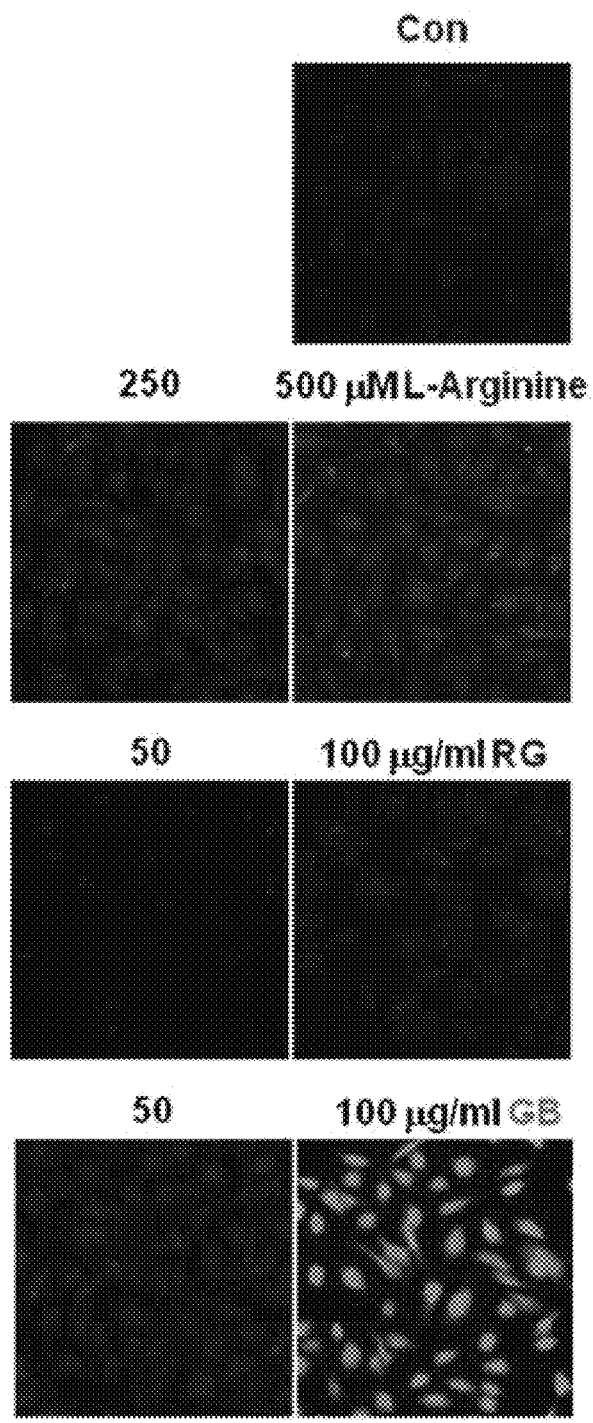
FIG. 21 shows confocal laser microscopic images showing NO generation facilitating effect of L-arginine, ginseng root extract and ginseng berry extract in endothelial cells
Figure 22:
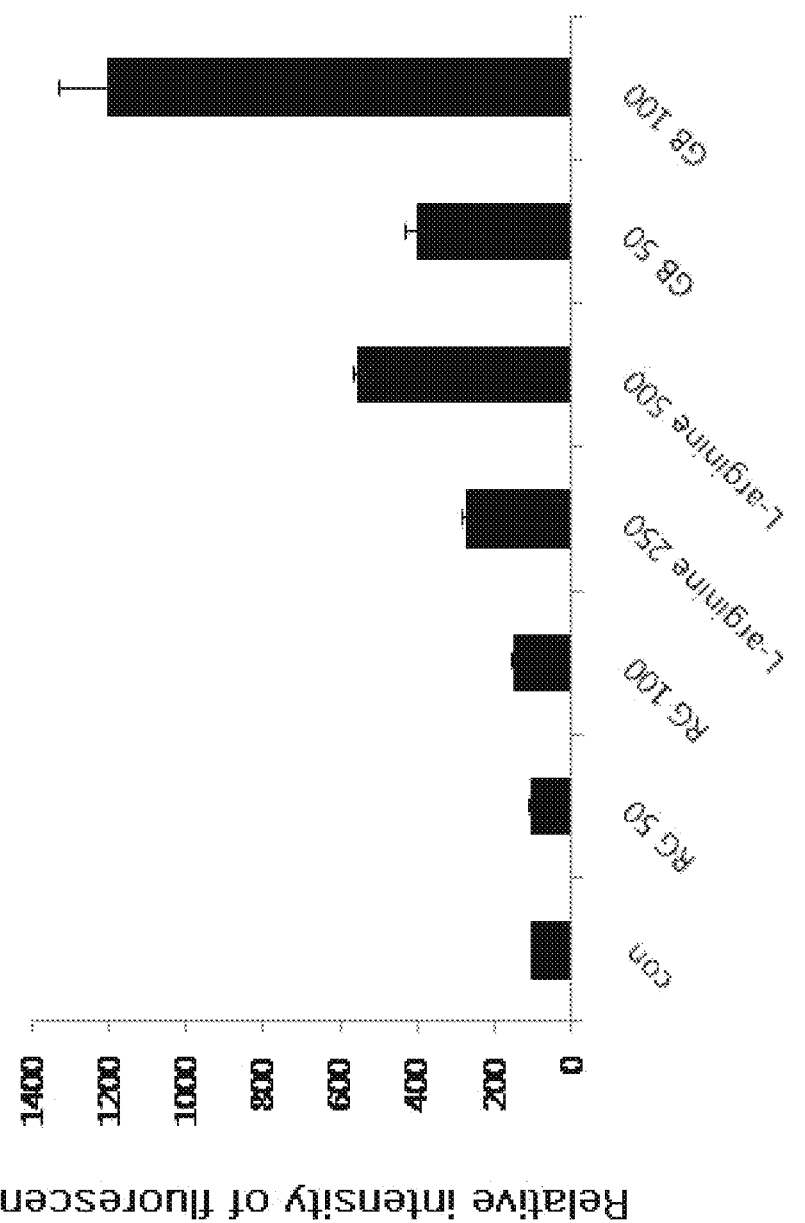
FIG. 22 shows NO generation facilitating effect of L-arginine, ginseng root extract and ginseng berry extract in endothelial cells as relative fluorescence intensity.

Increase of generation of NO, which is known as an important signal transduction substance related with penile erection, in endothelial cells was observed after treating with the ginseng berry extract. Experiment was carried out in a manner substantially the same as that of Test Example 2, but L-arginine was treated together with the ginseng root extract of Comparative Example 1 and the ginseng berry extract of Example 1. FIG. 21 shows confocal laser microscopic images (Atto Bioscience, USA), and FIG. 22 shows relative fluorescence intensity analyzed with the Image-Pro Plus v4.5 software (Media Cybernetics, San Diego, Calif., USA). In FIG. 21 and FIG. 22, Con stands for negative control group, RG for the group treated with the ginseng root extract of Comparative Example 1, GB for the group treated with the ginseng berry extract of Example 1, RG 50 for the group treated with 50 µg/mL of ginseng root extract, RG 100 for the group treated with 100 µg/mL of ginseng root extract, L-arginine 250 for the group treated with 250 µM of L-arginine, L-arginine 500 for the group treated with 500 µM of L-arginine, GB 50 for the group treated with 50 µg/mL of ginseng berry extract, and GB 100 for the group treated with 100 µg/mL of ginseng berry extract.

As seen from FIG. 21 and FIG. 22, when treated with the ginseng berry extract, the endothelial cells (HUVEC) exhibited significantly increased NO generation in the monolayer culture system, as compared to the control group, and the effect was concentration-dependent. At a concentration of 100 µg/mL, the ginseng root extract exhibited about 1.5 times increased NO generation with respect to the negative control group. L-Arginine, which is the substrate of nitric oxide synthase, increased NO generation by about 2.7 times and 5.5 times, at 250 µM and 500 µM, respectively. In contrast, the ginseng berry extract increased generation of NO, which is a blood vessel dilation signal transduction substance, by about 4 times and 12 times, with respect to the negative control group, at 50 µg/mL and 100 µg/mL, respectively. That is, the ginseng berry extract exhibited the best effect. The ginseng berry extract was about 8 times more efficient than the ginseng root extract, at a concentration of 100 µg/mL.

Therefore, it was confirmed that, intake of the ginseng berry extract results in increased NO generation in endothelial cells and, thus, can improve penile erection through dilation of blood vessels in the corpus cavernosum.

[Test Example 13] Synergic Effect of Facilitating NO Generation Upon Combined Use of Ginseng Berry Extract and L-Arginine It was observed whether a combination of L-arginine, which is known as the substrate of nitric oxide synthase, and the ginseng berry extract, which facilitates NO generation, provides a synergic effect of facilitating NO generation.

Endothelial cells were isolated from the umbilical cord and cultured, and NO generation in the cultured endothelial cells was measured. Specific experimental procedure was substantially the same as that of Test Example 12. The result is shown in FIG. 23.

Figure 23:
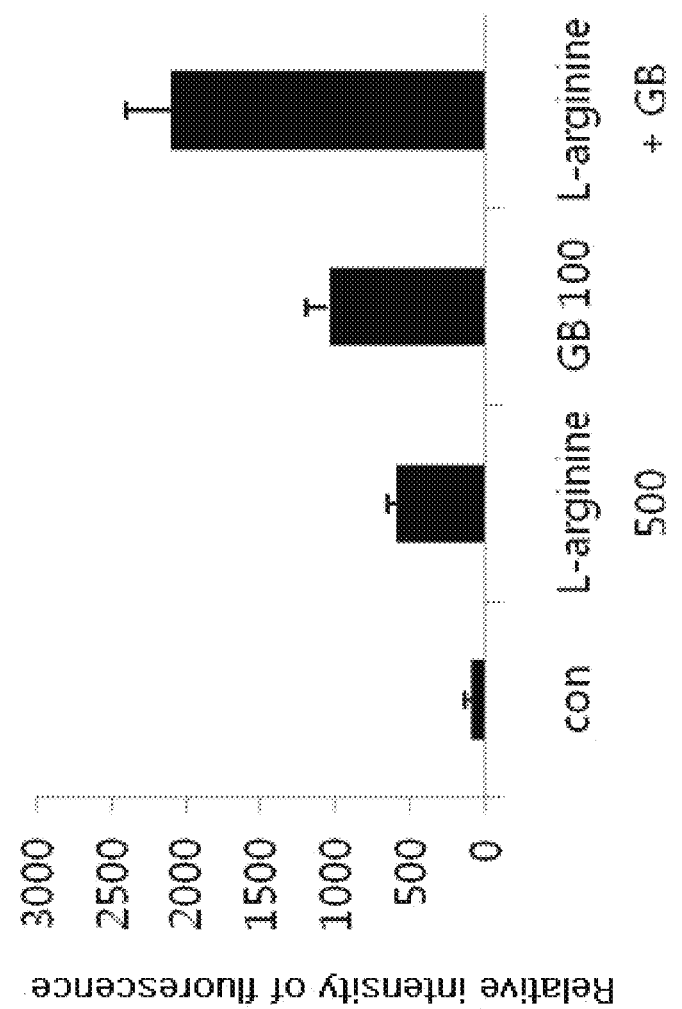
FIG. 23 shows synergic NO generation facilitating effect of ginseng berry extract and L-arginine as relative fluorescence.

In FIG. 23, Con stands for the control group, L-arginine 500 for the group treated with 500 µM of L-arginine, GB 100 for the group treated with 100 µg/mL of ginseng berry extract, and L-arginine+GB for the group treated with 500 µM of L-arginine and 100 µg/mL of ginseng berry extract.

As seen in FIG. 23, NO generation increased much more when the endothelial cells were treated with 100 µg/mL of ginseng berry extract and 500 µM L-arginine at the same time, than when they were treated with either of the two. That is, a synergic effect was confirmed.

From this result, it was confirmed that a combined use of L-arginine, which is the substrate of nitric oxide synthase, and the ginseng berry extract greatly increases NO generation and, thus, is effective in improving male sexual function through relaxation of the corpus cavernosum and improved and maintained penile erection.

[Test Example 14] Effect of Penile Cavernous Smooth Muscle

Since penile erection is a physiological phenomenon resulting from relaxation of the penile cavernous smooth muscle, the ginseng berry extract will be able to improve penile erection if it has superior effect of relaxing the cavernous smooth muscle. Therefore, the effect of the ginseng berry extract on the penile cavernous smooth muscle was evaluated for 4- to 6-month-old male New Zealand white rabbit.

Figure 24:
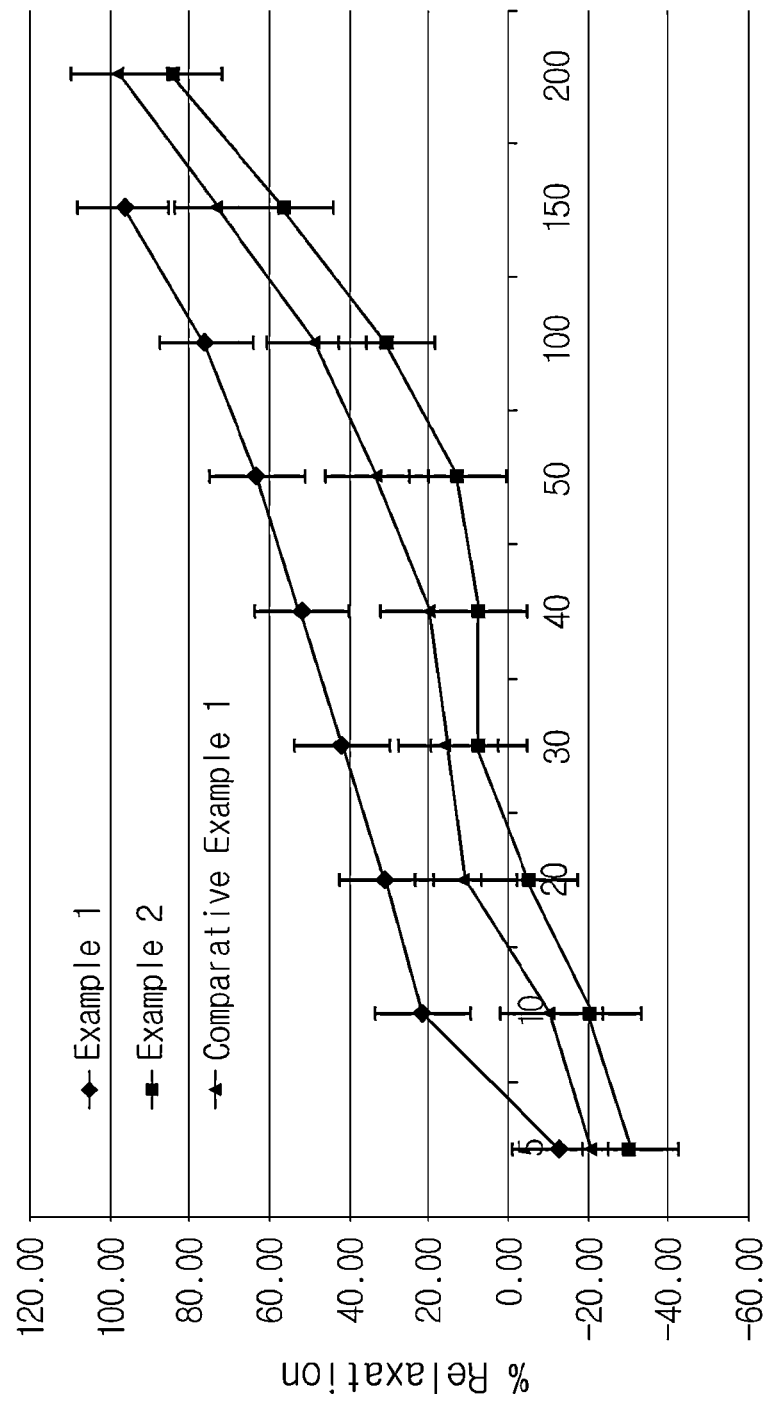
FIG. 24 shows relaxation of the penile cavernous smooth muscle by test substances.
Figure 25:
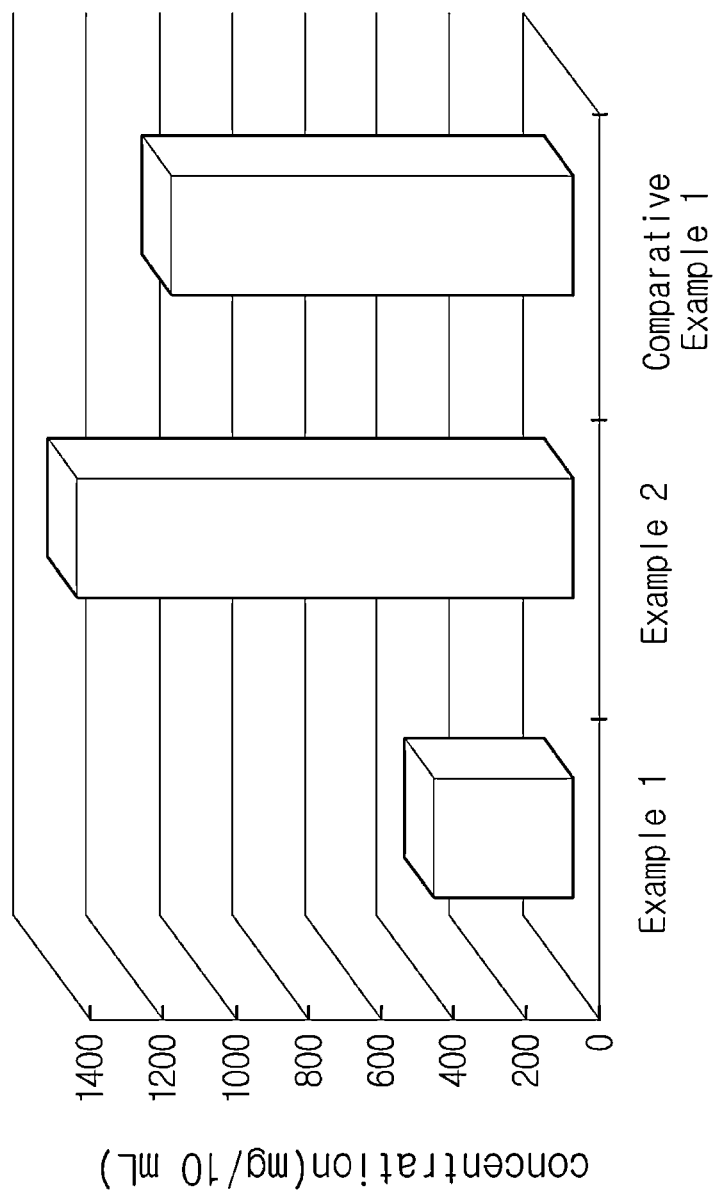
FIG. 25 compares the concentration (mg/10 mL) of test substances required to relax the penile cavernous smooth muscle contracted by phenylephrine to the same extent.

The whole penis of the rabbit of each group was excised and the penile cavernous smooth muscle was isolated in a physiological solution at low temperature under supply of a mixture gas of 95% oxygen and 5% carbon dioxide. The isolated penile cavernous smooth muscle was induced to contract using phenylephrine (PHE). The penile cavernous smooth muscle showing no or less than 15% of relaxation response to acetylcholine after deendothelialization was selected. Under a stabilized state of initial tension of 2 gm, PHE was injected to the selected penile cavernous smooth muscle and the level of contraction was observed. Contraction of less than 10% of the previous contraction for 2 consecutive times was determined as ideal tension. Under the ideal tension condition, 5-200 mg/mL of the ginseng berry extract of Example 1, the ginseng berry saponin concentrate of Example 2 and the ginseng root extract of Comparative Example 1 was injected to the penile cavernous smooth muscle which was contracted with PHE, respectively. After injection of the test substances, the relaxation of the penile cavernous smooth muscle was evaluated. The result is shown in FIG. 24. Further, the concentration (mg/10 mL) of each test substance (ginseng berry extract, ginseng berry saponin concentrate or ginseng root extract) necessary to relax the penile cavernous smooth muscle contracted by PHE 100% was compared. The result is shown in FIG. 25.

The ginseng berry extract of Example 1 showed superior, concentration-dependent effect of relaxing the penile cavernous smooth muscle. This effect was remarkably better than that of the ginseng root extract of Comparative Example 1 or the ginseng berry saponin concentrate of Example 2. Accordingly, it was confirmed that the ginseng berry extract of Example 1, which contains saponin together with other ingredients of ginseng berry, provides superior effect of relaxing the penile cavernous smooth muscle and thus improving penile erection and male sexual function.

Hereunder are described some formulation examples of a composition comprising the ginseng berry extract. However, they are described for illustrative purposes and are not intended to limit the scope of the present disclosure.

[Formulation Example 1] Injection 50 mg of the ginseng berry extract of Example 1, adequate amount of sterilized water for injection, and adequate amount of pH adjuster were mixed and filled in an ampule (2 mL) according to a common injection preparation method.

[Formulation Example 2] Liquid 100 mg of the ginseng berry extract of Example 1, 10 g of isomerized glucose, and 5 g of mannitol were dissolved in adequate amount of purified water. After adding adequate amount of lemon flavor and mixing the ingredients, purified water was added to make 100 mL. The resultant liquid was filled in a brown bottle and sterilized.

[Formulation Example 3] Soft Capsule 50 mg of the ginseng berry extract of Example 1, 80-140 mg of L-carnitine, 180 mg of soybean oil, 2 mg of palm oil, 8 mg of hardened vegetable oil, 4 mg of yellow beeswax, and 6 mg of lecithin were mixed and filled in a capsule according to a common method, with 400 mg per each capsule to prepare soft capsule.

[Formulation Example 4] Tablet 50 mg of the ginseng berry extract of Example 1, 200 mg of galactooligosaccharide, 60 mg of lactose, and 140 mg of maltose were mixed and granulated using a fluidized bed drier. Then, after adding 6 mg of sugar ester, the mixture was prepared into tablet using a tablet making machine.

[Formulation Example 5] Granule 50 mg of the ginseng berry extract of Example 1, 250 mg of anhydrous crystalline glucose, and 550 mg of starch were mixed, granulated using a fluidized bed granulator, and filled in a pouch.

[Formulation Example 6] Drink 50 mg of the ginseng berry extract of Example 1, 10 g of glucose, 0.6 g of citric acid, and 25 g of oligosaccharide syrup were mixed. After adding 300 mL of purified water, 200 mL of the mixture was filled in a bottle. Then, sterilization was carried out at 130° C. for 4-5 seconds.

[Formulation Example 7] Ginseng Berry 100% Extract

During the ginseng berry extract preparation process in Example 1, the extract was concentrated so that the solid content was 60% or higher. After aging at low temperature, 100% extract liquid product was prepared.

[Formulation Example 8] Pill 0.9 g of the ginseng berry extract of Example 1, 0.3 g of sugar, 1.91 g of starch, and 0.56 g of glycerin were mixed and prepared into pills using a pill making machine.

Although the preferred embodiments of the present disclosure have been disclosed for illustrative purposes, those skilled in the art will appreciate that various modifications, additions and substitutions are possible, without departing from the scope and spirit of the invention as disclosed in the accompanying claims.

What is claimed is:

1. A method for treating vascular inflammation of a subject in need thereof, comprising:
   administering an effective amount of a ginseng berry extract to said subject,
   wherein the ginseng berry extract is an ethanol extract is a saponin concentrate consisting of ginsenosides Rb1, Rb2, Rb3, Rc, Rd, Re, Rg1, and Rg2.

2. A method for treating vascular inflammation in a subject, comprising administering an effective amount of a ginseng berry extract to a subject in need of treatment for vascular inflammation, wherein the ginseng berry extract is a butanol fraction containing ginsenosides, and wherein the ginsenosides consist of ginsenosides Rb1, Rb2, Rb3, Re, Rd, Re, Rg1, and Rg2.

* * * * *